United States Patent
Chen

(10) Patent No.: US 11,357,432 B2
(45) Date of Patent: Jun. 14, 2022

(54) SYSTEM AND METHOD FOR NON-INVASIVELY MONITORING AUTONOMIC NERVE ACTIVITY

(71) Applicant: INDIANA UNIVERSITY RESEARCH & TECHNOLOGY CORPORATION, Indianapolis, IN (US)

(72) Inventor: Peng-Sheng Chen, Indianapolis, IN (US)

(73) Assignee: INDIANA UNIVERSTTY RESEARCH & TECHNOLOGY CORPORATION, Indianapolis, IN (US)

( * ) Notice: Subject to any disclaimer, the term of this patent is extended or adjusted under 35 U.S.C. 154(b) by 98 days.

(21) Appl. No.: 15/490,230

(22) Filed: Apr. 18, 2017

(65) Prior Publication Data

US 2017/0215752 A1   Aug. 3, 2017

Related U.S. Application Data

(63) Continuation of application No. PCT/US2015/056419, filed on Oct. 20, 2015.
(Continued)

(51) Int. Cl.
*A61B 5/00*   (2006.01)
*A61B 5/24*   (2021.01)
(Continued)

(52) U.S. Cl.
CPC .................. *A61B 5/24* (2021.01); *A61B 5/05* (2013.01); *A61B 5/4029* (2013.01);
(Continued)

(58) Field of Classification Search
CPC ...... A61B 5/0537; A61B 5/053; A61B 5/4872
(Continued)

(56) References Cited

U.S. PATENT DOCUMENTS 6,487,450 B1   11/2002   Chen
6,824,538 B2   11/2004   Chen
(Continued)

FOREIGN PATENT DOCUMENTS

WO   03099377 A1   12/2003
WO   2006094022 A2   9/2006
WO   2014089549 A1   6/2014

OTHER PUBLICATIONS

Adelman, et al., Small-Conductance Ca2+-Activated K+ Channels: Form and Function, Annual Review of Physiology, 2012, 74:245-269.
(Continued)

*Primary Examiner* — Daniel L Cerioni
(74) *Attorney, Agent, or Firm* — Faegre Drinker Biddle & Reath LLP

(57) ABSTRACT

System and methods for monitoring and/or controlling nerve activity in a subject are provided. In one embodiment, a system includes electrodes configured to be placed proximate to a subject's skin, and a signal detector configured to detect electrical signals using the electrodes. The system also includes a signal processor configured to receive the electrical signals from the signal detector, and apply a filter to the received electrical signals to generate filtered signals, the filter configured to attenuate at least signals having frequencies corresponding to heart muscle activity during a heartbeat. The signal processor is also configured to identify a skin nerve activity using the filtered signals, estimate a sympathetic nerve activity using the identified skin nerve activity, and further to generate a report indicative of the estimated sympathetic nerve activity. In some aspects, the
(Continued)

system further includes a signal generator to deliver the electrical stimulation to the subject's skin.

6 Claims, 14 Drawing Sheets

Related U.S. Application Data

(60) Provisional application No. 62/065,854, filed on Oct. 20, 2014, provisional application No. 62/158,323, filed on May 7, 2015.

(51) Int. Cl.
    *A61N 1/05*     (2006.01)
    *A61N 1/36*     (2006.01)
    *A61N 1/04*     (2006.01)
    *A61B 5/05*     (2021.01)
    *A61N 1/362*     (2006.01)
    *A61N 1/365*     (2006.01)

(52) U.S. Cl.
    CPC ............ *A61B 5/6877* (2013.01); *A61B 5/725* (2013.01); *A61N 1/0456* (2013.01); *A61N 1/0476* (2013.01); *A61N 1/0504* (2013.01); *A61N 1/0551* (2013.01); *A61N 1/36017* (2013.01); *A61N 1/36053* (2013.01); *A61N 1/3627* (2013.01); *A61N 1/36031* (2017.08); *A61N 1/36034* (2017.08); *A61N 1/36592* (2013.01)

(58) Field of Classification Search
    USPC .......................................................... 600/547
    See application file for complete search history.

(56) References Cited

U.S. PATENT DOCUMENTS

| | | | |
|---|---|---|---|
| 6,937,896 B1 | 8/2005 | Kroll | |
| 2003/0055349 A1 | 3/2003 | Yonce | |
| 2003/0078629 A1 | 4/2003 | Chen | |
| 2006/0004413 A1 | 1/2006 | Chen | |
| 2006/0004414 A1* | 1/2006 | Chen | A61B 5/04001 607/3 |
| 2006/0074451 A1* | 4/2006 | Chen | A61B 5/04001 607/3 |
| 2008/0015659 A1 | 1/2008 | Zhang et al. | |
| 2011/0218415 A1* | 9/2011 | Chen | A61B 5/04001 600/374 |
| 2012/0289856 A1 | 11/2012 | Motogi et al. | |
| 2013/0172967 A1 | 7/2013 | You | |
| 2014/0135886 A1 | 5/2014 | Cook et al. | |
| 2014/0214124 A1 | 7/2014 | Greiner et al. | |
| 2014/0276789 A1* | 9/2014 | Dandler | A61B 18/1492 606/41 |
| 2014/0316297 A1* | 10/2014 | Mccaughan | A61B 5/0537 600/547 |
| 2017/0063458 A1* | 3/2017 | Miyaho | H04B 10/116 |

OTHER PUBLICATIONS

Armour, Functional Anatomy of Intrathoracic Neurons Innervating the Atria and Ventricles, Heart Rhythm, 2010, 7(7):994-996.
Baron, et al., Sympathetic and Afferent Neurones Projecting Into Forelimb and Trunk Nerves and the Anatomical Organization of the Thoracic Sympathetic Outflow of the Rat, Journal of the Autonomic Nervous System, 1995, 53:205-214.
Bode, et al., Differential Effects of Defibrillation on Systemic and Cardiac Sympathetic Activity, Heart, 1998, 79:560-567.
Chen, et al., Role of the Autonomic Nervous System in Atrial Fibrillation: Pathophysiology and Therapy, Circ. Res., 2014, 114(9):1500-1515.
Choi, et al., Intrinsic Cardiac Nerve Activity and Paroxysmal Atrial Tachyarrhythmia in Ambulatory Dogs, Circulation, 2010, 121:2615-2623.
Chowdhury, et al., Surface Electromyography Signal Processing and Classification Techniques, Sensors, 2013, 13:12431-12466.
Converse, Jr., et al., Sympathetic Overactivity in Patients with Chronic Renal Failure, The New England Journal of Medicine, 1992, 327:1912-1918.
Donadio, et al., Skin Sympathetic Adrenergic Innervation: An Immunofluorescence Confocal Study, Ann. Neurol., 2006, 59:376-381.
Doytchinova, et al., Subcutaneous Nerve Activity and Spontaneous Ventricular Arrhythmias in Ambulatory Dogs, Heart Rhythm, 2015, 12(3):612-620.
Ellison, et al., Sympathetic Nerve Pathways to the Human Heart, and Their Variations, American Journal of Anatomy, 1969, 124:149-162.
Gatzoulis, et al., Electrical Storm is an Independent Predictor of Adverse Long-Term Outcome in the Era of Implantable Defibrillator Therapy, Europace, 2005, 7:184-192.
Grillner, The Motor Infrastructure: From Ion Channels to Neuronal Networks, Nature Reviews, 2003, 4:573-586.
Grossman, et al., Some Factors Affecting the Reliability of Surface Electromyography, Psychosomatic Medicine, 1966, 28(1):78-83.
Jiang, et al., Using Skin Sympathetic Nerve Activity to Estimate Stellate Ganglion Nerve Activity in Dogs, Heart Rhythm, 2015, 12(6):1324-1332.
Jung, et al., Circadian Variations of Stellate Ganglion Nerve Activity in Ambulatory Dogs, Heart Rhythm, 2006, 3:78-85.
Kawashima, The Autonomic Nervous System of the Human Heart with Special Reference to Its Origin, Course, and Peripheral Distribution, Anat. Embryol., 2005, 209:425-438.
Kligfield, et al., Recommendations for the Standardization and Interpretation of the Electrocardiogram, Part 1: The Electrocardiogram and Its Technology, Circulation, 2007, 115:1306-1324.
Komi, et al., EMG Frequency Spectrum, Muscle Structure, and Fatigue During Dynamic Contractions in Man, European Journal of Applied Physiology, 1979, 42:41-50.
Leimbach, Jr., et al., Direct Evidence from Intraneural Recordings for Increased Central Sympathetic Outflow in Patients with Heart Failure, Circulation, 1986, 73(5):913-919.
Leuenberger, et al., Control of Skin Sympathetic Nerve Activity During Intermittent Static Handgrip Exercise, Circulation, 2003, 108:2329-2335.
Luo, et al., A Comparison of Commonly Used QT Correction Formulae: The Effect of Heart Rate on the QTc of Normal ECGs, Journal of Electrocardiology, 2004, 37:81-90.
Marx, et al., Distribution of Sympathetic Fiber Areas in the Sensory Nerves of Forearm: An Immunohistochemical Study in Cadavers, Rom. J. Morphol. Embryol., 2011, 52(2):605-611.
McAuley, et al., Frequency Peaks of Tremor, Muscle Vibration and Electromyographic Activity at 10 Hz, 20 Hz and 40 Hz During Human Finger Muscle Contraction May Reflect Rhythmicities of Central Neural Firing, Experimental Brain Research, 1997, 114(3):525-541.
Middlekauff, et al., Independent Control of Skin and Muscle Sympathetic Nerve Activity in Patients with Heart Failure, Circulation, 1994, 90:1794-1798.
Morrison, Differential Control of Sympathetic Outflow, Am. J. Physiol. Regulatory Integrative Comp. Physiol., 2001, 281:R683-R698.
Moss, et al., Unilateral Cervicothoracic Sympathetic Ganglionectomy for the Treatment of Long QT Interval Syndrome, New England Journal of Medicine, 1971, 285:903-904.
Nademanee, et al., Treating Electrical Storm: Sympathetic Blockade Versus Advanced Cardiac Life Support-Guided Therapy, Circulation, 2000, 102:742-747.
Noll, et al., Role of Sympathetic Nervous System in Hypertension and Effects of Cardiovascular Drugs, European Heart Journal, 1998, 19(Suppl F):F32-F38.
Ogawa, et al., Left Stellate Ganglion and Vagal Nerve Activity and Cardiac Arrhythmias in Ambulatory Dogs With Pacing-Induced

(56) References Cited

OTHER PUBLICATIONS

Congestive Heart Failure, Journal of the American College of Cardiology, 2007, 50(4):335-343.
Onkka, et al., Sympathetic Nerve Fibers and Ganglia in Canine Cervical Vagus Nerves: Localization and Quantitation, Heart Rhythm, 2013, 10(4):585-591.
Ramsaroop, et al., Thoracic Origin of a Sympathetic Supply to the Upper Limb: The 'Nerve of Kuntz' Revisited, J. Anat., 2001, 199:675-682.
Robinson, et al., Estimating Sympathetic Tone by Recording Subcutaneous Nerve Activity in Ambulatory Dogs, J. Cardiovasc. Electrophysiol, 2015, 26(1):70-78.
Salmanpour, et al., Sympathetic Neural Recruitment Patterns During the Valsalva Maneuver, 33rd Annual International Conference of the IEEE EMBS, 2011, pp. 6951-6954.
Schalow, et al., Microanatomy and Number of Nerve Fibres of the Lower Intercostal Nerves with Respect to a Nerve Anastomosis. Donor Nerve Analysis. I (IV), Electromyogr. Clin. Neurophysiol, 1992, 32:171-185.
Schwartz, et al., Left Cardiac Sympathetic Denervation in the Management of High-Risk Patients Affected by the Long-QT Syndrome, Circulation, 2004, 109:1826-1833.
Seki, et al., Sympathetic Nerve Fibers in Human Cervical and Thoracic Vagus Nerves, Heart Rhythm, 2014, 11(8):1411-1417.
Shen, et al., Continuous Low-Level Vagus Nerve Stimulation Reduces Stellate Ganglion Nerve Activity and Paroxysmal Atrial Tachyarrhythmias in Ambulatory Canines, Circulation, 2011, 123:2204-2212.
Shen, et al., Low-Level Vagus Nerve Stimulation Upregulates Small Conductance Calcium Activated Potassium Channels in the Stellate Ganglion, Heart Rhythm, 2013, 10(6):910-915.
Swirski, et al., Leukocyte Behavior in Atherosclerosis, Myocardial Infarction, and Heart Failure, Science, 2013, 339(116):161-166.
Tan, et al., Neural Mechanisms of Paroxysmal Atrial Fibrillation and Paroxysmal Atrial Tachycardia in Ambulatory Canines, Circulation, 2008, 118(9):916-925.
Taniguchi, et al., Cutaneous Distribution of Sympathetic Postganglionic Fibers from Stellate Ganglion: A Retrograde Axonal Tracing Study Using Wheat Germ Agglutinin Conjugated with Horseradish Peroxidase, Journal of Anesthesia, 1994, 8(4):441-449.
Vaseghi, et al., Cardiac Sympathetic Denervation in Patients with Refractory Ventricular Arrhythmias or Electrical Storm: Intermediate and Long-Term Follow-Up, Heart Rhythm, 2014, 11(3):360-366.
Victor, et al., Effects of the Cold Pressor Test on Muscle Sympathetic Nerve Activity in Humans, Hypertension, 1987, 9:429-436.
Viskin, et al., The Response of the QT Interval to the Brief Tachycardia Provoked by Standing, Joirnal of the American College of Cardiology, 2010, 55:1955-1961.
Wilde, et al., Left Cardiac Sympathetic Denervation for Catecholaminergic Polymorphic Ventricular Tachycardia, New England Journal of Medicine, 2008, 358:2024-2029.
Yu, et al., Low-Level Transcutaneous Electrical Stimulation of the Auricular Branch of the Vagus Nerve: A Noninvasive Approach to Treat the Initial Phase of Atrial Fibrillation, Heart Rhythm, 2013, 0:1-8.
Zhou, et al., Spontaneous Stellate Ganglion Nerve Activity and Ventricular Arrhythmia in a Canine Model of Sudden Death, Heart Rhythm, 2008, 5:131-139.
Zipes, et al., Neural Modulation of Cardiac Arrhythmias and Sudden Cardiac Death, Heart Rhythm, 2006, 3(1):108-113.
PCT International Search Report and Written Opinion, PCT/US2015/056419, dated Jan. 6, 2016.

* cited by examiner

SYSTEM AND METHOD FOR NON-INVASIVELY MONITORING AUTONOMIC NERVE ACTIVITY

CROSS-REFERENCE TO RELATED APPLICATIONS

This application is a Continuation of PCT International Application No. PCT/US2015/056419 filed Oct. 20, 2015, which, claims priority to U.S. Provisional Application Ser. No. 62/065,854 filed on Oct. 20, 2014 and U.S. Provisional Application Ser. No. 62/158,323 filed on May 7, 2015, the contents of which are hereby incorporated herein by reference for all purposes.

GOVERNMENT RIGHTS

This invention was made with government support under HL071140 and TR002208 awarded by National Institutes of Health. The government has certain rights in the invention.

BACKGROUND

The present disclosure relates generally to systems and methods for monitoring nerve activity and, in particular, to systems and methods for non-invasive monitoring and/or controlling nerve activity using cutaneous and/or subcutaneous electrodes.

Many diagnostic and treatment methods in the fields of medicine and biology rely on measurements of nerve activity in patients and test subjects. Nerve activity in humans and other animals generates electrical signals that are detectable by electronic equipment such as oscilloscopes and other electrical signal processing devices. In order to detect the nerve activity, one or more electrical conductors, or electrodes, are placed in proximity to the nerves being measured. The electrodes may receive the electrical signals for further medical analysis. In addition, various medical treatment methods also use electrodes to deliver electrical signals to the nerves in order to induce a response in the patient.

Cardiac care is one particular area of medical treatment that heavily utilizes measurement of nerve activity. Activity in the autonomic nervous system controls the variability of heart rate and blood pressure. The sympathetic and parasympathetic branches of the autonomic nervous system modulate cardiac activity. Elevated levels of sympathetic nerve activity ("SNA") are known to be correlated with heart failure, coronary artery disease, and may be associated with the initiation of hypertension. SNA is also thought to be important as a predictor of heart rhythm disorders, including sudden cardiac death.

Sympathetic nerve activity measurements have many medical uses including identification of specific conditions or determination of a treatment course. For example, previous studies have shown that directly recorded stellate ganglion nerve activity ("SGNA") immediately precedes heart rate acceleration and spontaneous cardiac arrhythmias. However, one challenge to measuring nerve activity is that the magnitude of electrical signals in the sympathetic nerves is relatively low, while various other electrical signals present in a patient provide noise that may interfere with isolation and detection of the sympathetic nerve activity. For example, in the human body and the bodies of many animals the electrical activity in the cardiac muscle generates electrical signals with much greater amplitudes than the amplitudes of electrical signals in the nerves. Other muscles in the body can also generate large electrical signals, but the cardiac muscle contractions in a heartbeat occur continuously during any nerve monitoring procedure, and the electrical signals from the cardiac muscle contractions present difficulties in monitoring the lower amplitude signals in the nerve fibers.

In general, sympathetic nerve activity is measured by bringing one or more electrodes into contact with a target nerve that is insulated from the surrounding tissue, and then the grouped action potentials are measured. However, in addition to the fact that measured signals are in microvolts, a number of factors, including differences in contact between the nerve and the electrodes, could lead to differences in the amplitude of the recorded signal. In addition, such procedures are generally invasive in order to gain access to the target nerves. For example, direct recording from the stellate ganglion would necessitate an incision into the pleural space of the chest.

Cardiac sympathetic innervation derives from the paravertebral cervical and thoracic ganglia. In particular, the stellate (cervicothoracic) ganglion is a major source of cardiac sympathetic innervation, formed by the fusion of the inferior cervical ganglion and the first thoracic ganglion. Clinical studies have shown that the left stellate ganglion is an important component in cardiac arrhythmogenesis. Specifically excessive sympathetic outflow from the stellate ganglion is a major cause of heart rhythm problems, and may, in part, account for the pathophysiology of heart failure.

Reducing the sympathetic outflow by stellate ganglion resection has been known to be anti-arrhythmic. In addition, stellate ganglion ablation has also been used as a method for preventing sudden death in patients with life threatening ventricular arrhythmias. However, these approaches generally require surgeons to enter the thoracic cavity of a subject in order to find and destroy the stellate ganglion. As such, need for an invasive procedures has prevented widespread use, and particularly with respect to patients with less than lethal cardiac arrhythmia.

In a previous study, it was found that vagal nerve stimulation can reduce SGNA and control atrial fibrillation. However, the vagal nerve is a vital structure responsible for a variety of functions including heart rate, gastrointestinal peristalsis, sweating, muscle movements, and so on. Gaining access to the vagal nerve requires an expert neurosurgeon or vascular surgeon, and the procedure is considered to be very delicate involving high risk. If the vagal nerve is accidentally damaged, the consequences to the subject body would be severe. As such, several clinical studies involving vagal nerve stimulation have reported a number of serious adverse effects and even death.

Given the above, there is a continuing need for systems and methods capable of monitoring and/or controlling various cardiac and other conditions using limited or non-invasive procedures that minimize risk and complications.

SUMMARY

The present disclosure overcomes the drawbacks of previous technologies by providing a system and methods for monitoring and/or controlling nerve activity in a subject. In particular, a novel non-invasive, or minimally invasive approach is introduced that may be used in the diagnosis and treatment of various cardiac and other medical conditions. As will become apparent from the following description, such approach can significantly reduce potential risk and complications associated with previous invasive procedures, thus improving the possibility of clinical translation.

In one aspect of the present disclosure, a system monitoring nerve activity in a subject is provided. The system includes a plurality of electrodes configured to be placed in locations proximate to a subject's skin, and a signal detector configured to detect electrical signals from the subject using the plurality of electrodes. The system also includes a signal processor configured to receive the electrical signals from the signal detector, and apply a filter to the received electrical signals to generate filtered signals, the filter configured to attenuate at least signals having frequencies that correspond to heart muscle activity during a heartbeat. The signal processor is also configured to identify a skin nerve activity using the filtered signals, and estimate a sympathetic nerve activity using the identified skin nerve activity. The signal processor is further configured to generate a report indicative of the estimated sympathetic nerve activity.

In another aspect of the present disclosure, a method for monitoring nerve activity in a subject is provided. The method includes amplifying electrical signals received from a plurality of electrodes placed in locations proximate to a subject's skin to generate a plurality of amplified signals, and applying a filter to the plurality of electrical signals to generate a plurality of filtered signals, the filter configured to attenuate at least signals having frequencies that correspond to heart muscle activity during a heartbeat. The method also includes identifying a skin nerve activity using the plurality of filtered signals, and estimating a sympathetic nerve activity using the identified skin nerve activity. The method further includes generating a report indicative of the estimated sympathetic nerve activity.

In yet another aspect of the present disclosure, a method for controlling nerve activity in a subject is provided. The method includes placing a plurality of electrodes at locations proximate to nerves innervating a subject's skin, and generating an electrical stimulation configured to remodel at least one neural structure. The method also includes delivering the electrical stimulation to the subject's skin using the plurality of electrodes to control a sympathetic nerve activity.

In yet another aspect of the present disclosure, a method for controlling nerve activity in a subject is provided. The method includes acquiring electrical signals from locations proximate to a subject's skin using a plurality of electrodes placed thereabout, amplifying the electrical signals to generate a plurality of amplified signals, and applying a filter to the amplified signals to generate a plurality of filtered signals, the filter configured to attenuate at least signals having frequencies that correspond to heart muscle activity during a heartbeat. The method also includes identifying a skin nerve activity using the plurality of filtered signals, and estimating a sympathetic nerve activity using the identified skin nerve activity. The method further includes generating, based upon the estimated sympathetic nerve activity, an electrical stimulation configured to remodel at least one neural structure, and delivering the electrical stimulation to the subject's skin using the plurality of electrodes to control the estimated sympathetic nerve activity.

The foregoing and other advantages of the invention will appear from the following description.

DETAILED DESCRIPTION

Figure 1:
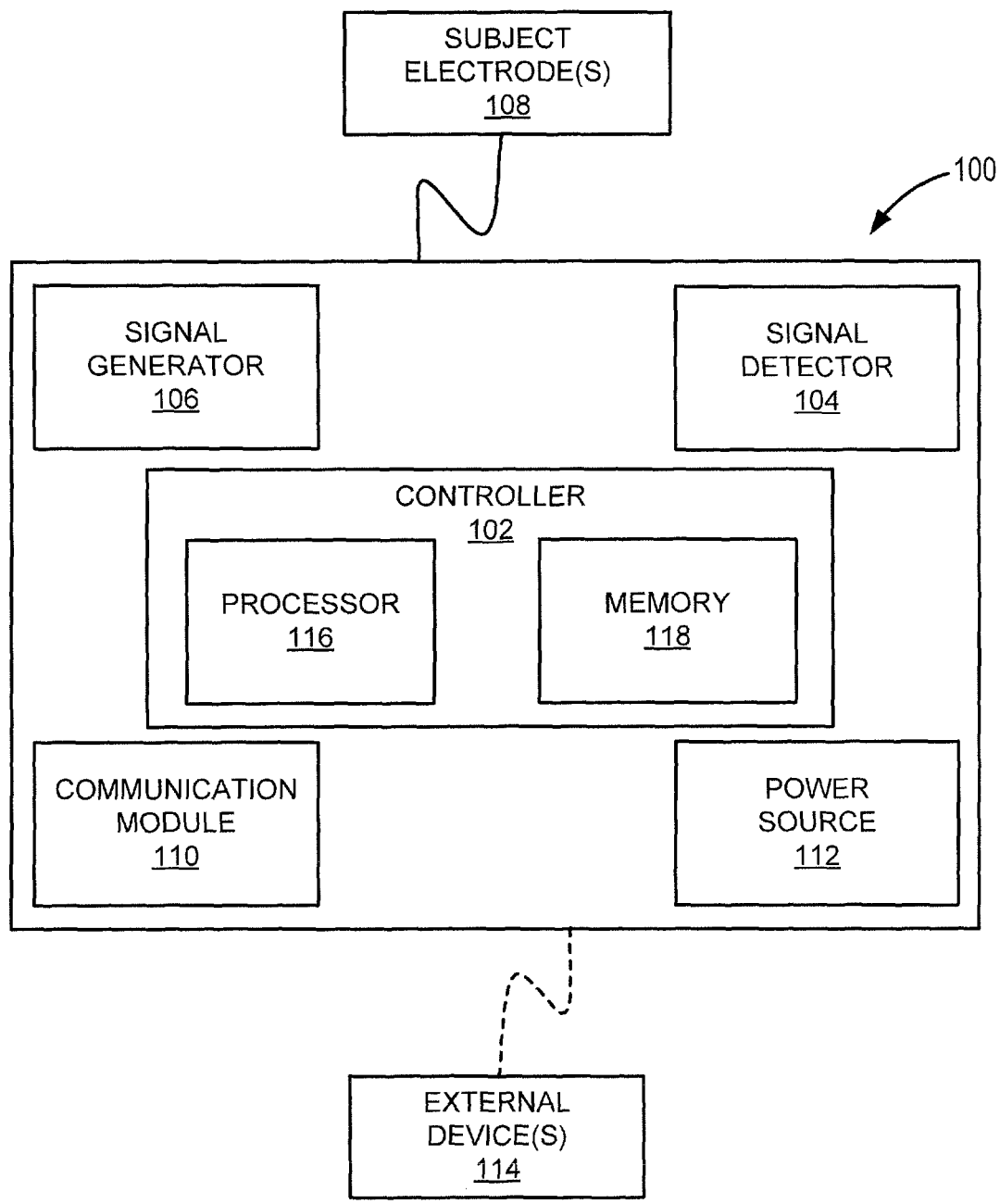
FIG. 1 a schematic diagram of an example system for monitoring and/or controlling nerve activity of a subject, in accordance with aspects of the present disclosure.

Excessive sympathetic outflow from the stellate ganglion is believed to be a major cause of heart rhythm problems, and may in part account for the pathophysiology of heart failure. Some treatments for managing heart rhythm have included medications as well as surgical removal or ablation of the stellate ganglion. Alternatively, it was recently discovered by the inventors that stimulating the vagal nerve can induce stellate ganglion remodeling, thus decreasing sympathetic nerve activity and providing therapeutic effects, such as controlling ventricular rate during atrial fibrillation. However, the vagal nerve is an anatomical structure that is critical to many bodily functions. As such, vagal nerve stimulation procedures carry a significant risk and require a high degree of technical expertise. In addition, the need for accessing the vagal nerve often limits practical clinical usage. As such, safer techniques directed to less critical structures that can achieve comparable therapeutic effects are desirable. Therefore, the present disclosure introduces a novel approach for monitoring and/or controlling sympathetic nerve activity of a subject, that is achievable in a non-invasive or minimally invasive manner.

In particular, in some aspects of the disclosure, sympathetic nerve activity can be obtained by measuring skin nerve activity ("SKNA"). That is, electrical signals acquired using cutaneous and/or subcutaneous electrodes, placed at various locations about a subject's skin, may be used to estimate sympathetic nerve activity, such as stellate nerve activity ("SGNA"). In this manner, information useful in the diagnosis and treatment of various medical conditions, such as heart rhythm problems, may be generated without need for invasive and more risky procedures. For instance, information associated with SGNA, and other nerve activities of a subject, may be used to predict cardiac arrhythmia, as well as provide a risk stratification.

In addition, in contrast to previous vagal nerve stimulation techniques, disclosed herein are a system and methods for controlling sympathetic nerve activity using electrical simulations delivered via cutaneous and/or subcutaneous electrodes. In this manner, specific neural structures, such as the stellate ganglion, may be stimulated or remodeled to achieve therapeutic effects without the risks involved in invasive procedures, such as vagal nerve stimulation or surgical resection of the stellate ganglion.

The description below and the accompanying figures provide a general understanding of the environment for system and methods disclosed herein as well as the details for the system and methods. In the drawings, like reference numerals are used throughout to designate like elements. As used herein, the term "electrode" refers to an electrical conductor that is configured to establish an electrical contact with biological tissue such as tissue in a patient or test subject. As used herein, the term "arrhythmia" refers to any abnormal activity in the heart of a subject. Examples of arrhythmia include, but are not limited to, tachycardia, bradycardia, atrial flutter, atrial fibrillation, premature contractions, ventricular fibrillation, heart palpitations, and cardiac arrest.

As used herein, the terms "proximity" and "proximate" when used to describe the location of an electrode with respect to the skin of a test subject mean that the electrode is placed in a location on the surface (epidermis) of the skin or under the skin near the hypodermis to enable the electrode to receive electrical signals corresponding to nerves that innervate the skin. For example, in a cutaneous configuration, the electrode is placed in contact with a surface of the skin of the test subject, with some embodiments using an electrical conductor such as a conductive gel to promote electrical contact between the electrode and the skin. In a subcutaneous configuration, the electrode is implanted under the skin of the test subject to enable the electrodes to receive electrical signals in nerves that innervate the hypodermis. In a subcutaneous configuration, the electrode is either in contact with the hypodermis or located within a short distance from the hypodermis, such as under a layer of adipose tissue that is under the skin.

As used herein, the term "cutaneous" as applied to use of electrodes refers to placing electrodes on the surface of the skin of a subject without puncturing the skin of the subject. As described below, the cutaneous electrodes detect electrical activity associated with nerves that are proximate to the skin of the subject, including sympathetic nerves in the autonomic nervous system that innervate the skin.

As used herein, the term "subcutaneous" as applied to use of electrodes refers to placing electrodes entirely underneath the skin with leads from the electrodes being electrically connected to a device that is placed in the body of the test subject, such as an internal pacemaker, defibrillator, or cardiac resynchronization device. The subcutaneous electrodes described herein are different than electrodes that are used in prior art microneurography procedures. First, the subcutaneous electrodes are completely under the skin, with no portion of the electrode or lead extending through the skin. Second, the subcutaneous electrodes do not have to be placed in close proximity to a particular nerve fiber to be used in detection of electrical signals from nerve activity. Third, the subcutaneous electrodes are shaped with a blunt contact surface without the sharp needle tips of microneurographic electrodes, which enables the subcutaneous electrodes to remain under the skin of an ambulatory subject for long term monitoring of nerve activity without injuring the subject. Fourth, the metal housing of an implanted device can be used to house subcutaneous electrodes in some embodiments. In the latter situation, no additional electrodes are needed.

In both the cutaneous and subcutaneous configurations described above, the electrodes are located proximate to nerves that innervate the skin. As is known in the medical art, many nerves that innervate the skin are part of the sympathetic nervous system, which is in turn part of the autonomic nervous system in humans and many animals. Different nerve fibers in the sympathetic nervous system also innervate cardiac tissue as well as other muscles and organs in the body. For example, the sympathetic nervous system is associated with the "fight or flight" response where the sympathetic nervous system activity increases and the pupils dilate, the heart rate increases, bronchioles in the lungs dilate, blood vessels near the surface of the skin constrict, and the sweat glands secrete sweat at a higher rate. The sympathetic nervous system is also associated with the "sympathetic outflow" process that occurs when a subject awakens from sleep. While the sympathetic nervous system includes a large number of nerve bundles that innervate different parts of the body in a subject, the nerves in the sympathetic nervous system are associated with each other and the level of activity in one nerve fiber often corresponds to the level of activity in other nerve fibers in the sympathetic nervous system.

Turning to FIG. 1 a non-limiting example of a system 100, for use in accordance with aspects of the present invention, is shown. In general, the system 100 may include a controller 102, a signal detector 104, a signal generator 106, and a plurality of electrodes 108. In some implementations, the system 100 may also include a communication module 110 and a power source 112. The system 100 may be an external system, a portable device, a wearable system, an implantable device, a partially implantable device, a pacemaker, and so forth.

In some aspects, the system 100 may operate autonomously or semi-autonomously, or may read executable software instructions from a computer-readable medium (such as a hard drive, a CD-ROM, flash memory and the like). The system 100 may also receive data or instructions from a user or clinician, via an input configured on the system 100, or any another source logically connected to the system 100. For instance, system 100 may receive input, data, or instructions from external device(s) 114, as shown in FIG. 1, as well as from a database, a storage server, a cloud, the internet, and other locations, using a wired or wireless communication. Examples external devices 114 may include personal computers, laptops, tablets, smartphones, personal digital assistant ("PDA") or other devices or systems.

In addition carrying out steps for operating system 100, the controller 102 may be configured to monitor and/or control sympathetic nerve activities for diagnosing and treating a medical condition of a subject. For example, the controller 102 may be configured to monitor and/control stellate ganglion activity. In some aspects, the controller 102 may be configured to direct the signal detector 104 to acquire electrical signals from electrodes 108 placed about a subject, for example, cutaneously or subcutaneously, or both. The controller 102 may also be configured to direct the signal generator 106 to generate and deliver electrical stimulations to target tissues, nerves, plexi, and other locations or regions of the patient's body, using the electrodes 108. In some aspects, the controller 102 may receive manual instructions from an operator externally, or may cause electrical stimulations to be generated and delivered based on internal calculations and programming, or based on measurements or estimations of various nerve activities.

In general, the controller 102 shown in FIG. 1 may include a processor 116, a memory 118, as well as other hardware components. In particular, the processor 116 can include one or more microcontrollers, microprocessors, and the like, and be capable of performing a number of processing steps, in accordance with aspects of the present disclosure, as described in detail below. The memory 118 may include various memory portions where a number of types of data (e.g., internal data, external data instructions, software codes, status data, diagnostic data, etc.) may be stored. The memory 118 may include one or more of random access memory ("RAM"), dynamic random access memory ("DRAM"), electrically erasable programmable read-only memory ("EEPROM"), flash memory, and the like. In some implementations, the controller 102 may be included in the same housing as the signal detector 104, signal generator 106, communication module 110 and power source 112. Alternatively, the controller 102, along with other components of the system 100 may be housed separately, as separate or stand-alone components, devices or systems.

For example, in one embodiment, the controller 102 may be a mobile electronic device, such as a smartphone or tablet, a personal computer ("PC"), or any suitable computing device that includes a central processing unit ("CPU") with one or more cores and a graphical processing unit ("GPU"). The CPU and optionally the GPU execute stored software instructions stored in memory 118 to apply filters to acquired data samples and to perform other signal processing functions on the data samples. For example, software configured for signal processing tasks in processor 116 may include the PowerLab data acquisition software commercially available from ADInstruments of Sydney, Australia. In some aspects, the controller 102 may include one or more digital logic devices, including application specific integrated circuits ("ASICs"), field programmable gate arrays ("FPGAs"), and digital signal processor ("DSP") devices. In addition, in some portable or implantable device embodiments of the system 100, the controller 102 may include low-power digital logic devices that enable long-term operation between battery recharge or replacement.

As described, the signal detector 104 is configured to acquire various electrical signals from the subject, while the signal generator 106 is configured to deliver the electrical stimulations to the subject using various combinations of electrodes 108. In some implementations, the signal detector 104 may include one or more amplifier capable of amplifying voltage signals, or differential voltage signals, received from the electrodes 108. The signal detector 104 may also include a sampler that generates digitized samples of amplified signals via an analog to digital converter ("ADC") for further processing by the processor 116. By way of example, the signal amplifier and sampler may be configured to amplify signals in a frequency range of 1 Hz to 5,000 Hz and to generate digital samples of the amplified signals at a rate of 10,000 samples per second. In one example embodiment, the signal amplifier and sampler can be an ML 135 dual-bio amplifier that is manufactured by the ADInstruments of Sydney, Australia. In some aspects, the signal amplifier and sampler may be electrically connected to the electrodes 108 in a configuration that includes at least one reference electrode and two input signal electrodes. On the other hand, the signal generator 106 may include a variety of hardware, circuitry and components for generating continuous or intermittent electrical stimulations, in accordance with aspects of the present disclosure, including any number of voltage and current sources.

In accordance with aspects of the disclosure, the electrodes 108 may be configured to engage a subject cutaneously and/or subcutaneously, and may be arranged in any number of lead configurations. For instance, the electrodes 108 may be electrically connected, or proximate to various locations about a subject's body to enable effective detection of electrical signals, such as electric signals from nerves that innervate the skin locations. In some configurations, the electrodes 108 may be arranged to facilitate monitoring of both nerve activity and cardiac activity. In addition, electrodes 108 may be configured to deliver continuous or intermittent electrical stimulations generated by signal generator 106. The electrodes 108 may also be configured to measure other signals besides nerve activity, including heart rate, respiration, and so forth.

In some aspects, the communication module 110 may be configured to facilitate communications between the system 100 and various devices. In particular, the communication module 110 may be capable of providing transmission and reception of electronic signals to and from the external device(s) 114 and other locations using a wired or wireless connection. The communication module 110 may include any hardware, software, firmware, and in some aspects be capable of telemetry, Bluetooth or other wireless communication protocol. In some implementations, the communication module 110 may also be configured to receive user input directly, such as operational instructions, as well as provide various information, in any form, related to operational parameters, signals detected and/or processed, such as cardiac activity, nerve activity, and the like. The communication module 110 may also be configured to provide information regarding provided electrical stimulations. In some aspects, the communication module 110 may include capabilities for delivering audio signals or queues, as well as visual outputs, for example, using a monitor, LCD display, and other output component configured therein.

Referring again to FIG. 1, in some aspects, the processor 116 of system 100 may include digital logic device that can perform a number of signal processing steps to identify nerve activity in data samples received from the signal detector 104. Specifically, the processor 116 may be configured to estimate a sympathetic nerve activity, such as a stellate ganglion activity, based on identified skin nerve activity, for example, using determined signal correlations stored in memory 118.

As described in more detail below, the electrical activity in the nerves that innervate the skin occurs at higher frequencies and lower amplitudes compared to the electrical signals generated in the cardiac muscle during a heartbeat. As such, processor 116 may be configured to identify and monitor the electrical signals corresponding to specific signals in the subject, such as nerve or cardiac activity, by processing data samples received from the signal detector 104. That is, the processor 116 may apply appropriate filters, such as low-pass filters, high-pass filters, or band-pass filters, to the data to obtain signals of interest. The processor 116 may also scale, multiply or integrate various measured signals.

For example, a 3 dB high-pass filter lower with a cutoff frequency adjustable in a range of approximately 100-1 kHz may be utilized. Selection of the proper high-pass setting might require consideration of signal specificity and acceptable sensitivity. For instance, a high-pass cutoff frequency of 150 Hz would be sufficient to attenuate most the lower frequency signals from cardiac muscle activity and electrical signals from other muscles in the subject typically observed, but not all muscle noise. On the other hand, a cutoff at 700 Hz would be more specific to nerve activity, as the muscle noise does not generate signals with frequencies above 500 Hz, but such filter setting would result in a reduced measurement sensitivity. In some preferred embodiments, the high-pass filter cutoff frequency may be between 150 Hz and 700 Hz, although other values may be possible.

In some aspects, data samples may also be processed using a low-pass filter, for example, with a cutoff frequency approximately in a range between 10 Hz and 150 Hz in order to detect cardiac activity. Alternatively, a band-pass filter may be applied to monitor the ECG of the subject using the amplified signal samples from the signal detector 104. For example, the band-pass filter may have a lower cutoff frequency of approximately 0.5 Hz and an upper cutoff frequency of approximately 100 Hz. In some aspects, the same pair of electrodes 108, such ECG patch electrodes, may be used to simultaneously record the ECG and skin nerve activity from the surface of thoracic skin. In such case, the same signals may be low-pass filtered for selective ECG signals and high-pass filtered for SKNA signals. Additionally, where an alternating current ("AC") electrical signal is used to supply power to one or more components in system 100, a band-pass filter also includes a notch-filter that attenuates frequencies near the primary frequency of the AC signal, such as 50 Hz or 60 Hz.

In addition to monitoring the electrical signals that correspond to the nerve activity and optionally the ECG, the processor 116 may be configured to analyze the signals to identify changes in the level of nerve activity, such as a skin or sympathetic nerve activity, and take an appropriate action in response to changes in the nerve activity. For example, in one configuration the processor 116 may identify a baseline of a nerve activity over time including an average amplitude and variation of the electrical signals that correspond to a nerve activity.

In some aspects, the processor 116 may be further configured to determine or identify a subject condition, for example, using identified nerve activity or changes thereof. Based on the subject condition, processor 116 may then identify an appropriate treatment protocol, either autonomously or by way of user input, to include intermittent periods of electrical stimulation, or "ON" periods, as well as time intervals of non-stimulation, or "OFF" periods, arranged in any timing pattern. In some aspects, a treatment protocol may include intermittent periods of electrical stimulation separated by periods of non-stimulation, where the intermittent periods include electrical stimulation described by parameters including one or more duration, intensity, frequency, pulse width or waveform, other any combination thereof. The intermittent "ON" and "OFF" periods may be unequal in duration and, in this regard, the process may be referred to as asynchronous. The processor 116 may then direct the signal generator 106 to deliver the treatment protocol via electrodes 108.

In one non-limiting example, intermittent periods of electrical stimulation may be delivered using electric pulses with a frequency between 0.1 Hz and 20 Hz, pulse widths between 0.1 milliseconds and 5 milliseconds, and stimulation intensities in a range between 0.1 milliAmperes to 5 milliAmperes, although other values are possible. In some applications, a treatment protocol may include brief ON periods, for example, of 1 to 20 seconds in duration, and long OFF periods, for example, lasting 60 seconds to 15 minutes in duration, although other values may be possible. Advantageously, such treatment protocol would reduce a stellate ganglion activity by inducing stellate ganglion remodeling or causing stellate ganglion tissue damage. Specifically, short and intermittent pulses would cause sufficient stellate ganglion damage during the ON-time and result in reduced nerve firing during the OFF-time.

In some aspects, a treatment may be configured such that a reduced activity of neural structures, including sympathetic structures, can be achieved. In other aspects, the treatment protocol may be customized by taking into consideration a determined baseline neural activity, such as a sympathetic nerve activity, or a parasympathetic nerve activity, and a target neural activity or target ventricular rate.

The cardiac activity of the subject is not the only type of medical event that corresponds to changes in the nerve activity in the sympathetic nervous system. Other changes in the level of nerve activity in the subject can correspond to the onset of symptoms related to various other medical conditions including, but not limited to, hyperhidrosis (sweaty palms), paralysis, stroke, diabetes, seizure disorder, syncope, disturbance of consciousness, hyperthyroidism, hypertension and neuromuscular diseases. Other areas of treatment include biofeedback monitoring performed by neurologists to control neuropsychiatric disorders. In such approaches, system 100 may be used to identify a suitability of a patient to receive a therapy aimed at modifying an identified nerve activity for treatment of certain medical conditions or diseases, such as hypertension and cardiac arrhythmia. For example, a neuromodulation therapy, such as renal sympathetic denervation, may be performed to reduce or modify sympathetic nerve activity. Monitored nerve activity may also be desirable for providing guidance while performing a procedure, and also for determining an effectiveness of a treatment after delivery with reference to a difference in the identified nerve activity. Additionally, another area includes lie-detection tests, because the sympathetic nerve activation is the mechanism that regulates sweating, pupil contraction, and other physiological responses that are measured during lie detector tests. Thus, the system 100 identifies changes in the nerve activity of the subject that correspond to changes in cardiac activity and the onset of symptoms in different diseases and conditions that affect the subject.

Figure 2:
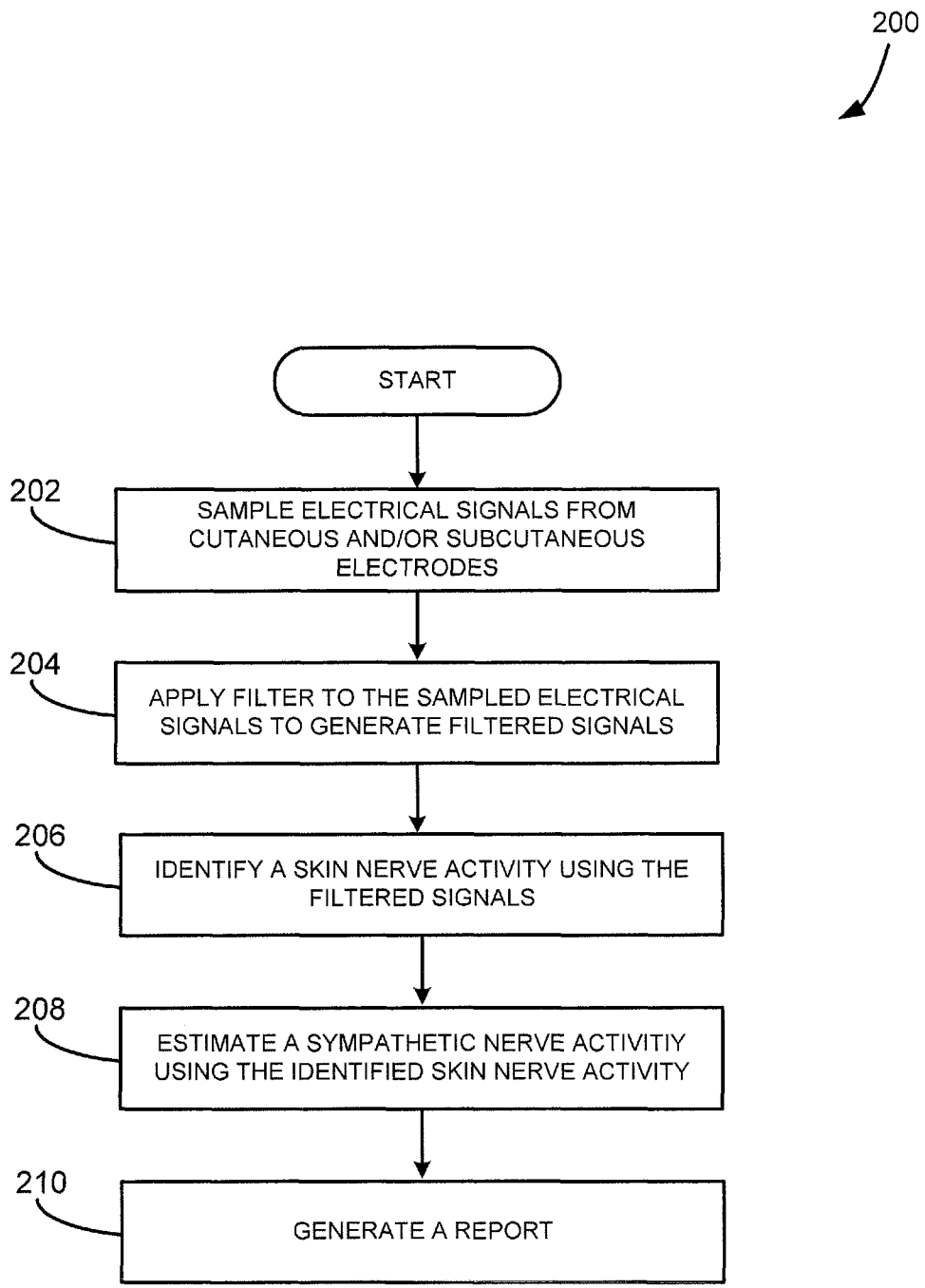
FIG. 2 shows steps of an example process for monitoring nerve activity in a subject, in accordance with aspects of the present disclosure.

Turning now to FIG. 2, the steps of a process 200 for monitoring nerve activity in a subject using cutaneous or subcutaneous electrodes recording electrical activity in nerves that innervate the skin, are shown. In some aspects, the process 200 may be carried out using a system 100, as described with reference to FIG. 1. The process 200 may begin at process block 202 with receiving electrical signals sampled using cutaneous and/or subcutaneous electrodes, for example using system 100, as described above. In some configurations, three or more electrodes, may be placed on the skin of the subject in a cutaneous configuration. Electrodes may be additionally, or alternatively implanted under the skin of the subject in a subcutaneous configuration, although other arrangements are possible. Referring specifically to the system 100 of FIG. 1, in some aspects, the signal detector 104 may amplify differential voltage signals that are received from the electrodes and generate digitized samples of the signals.

Process 200 continues with application of a filter to the sampled electrical signals to generate filtered signals, as indicated by process block 204. In some aspects, the filter may be configured to attenuate at least signals having frequencies that correspond to heart muscle activity during a heartbeat. Other signal filtering, as well as processing steps may also be possible at process block 204, including scaling, multiplying, or integrating the signals sampled at process block 202. In some aspects, a high-pass filter may be applied to the processed signal samples. Specifically, the high-pass filter may have a lower cutoff frequency in a range of 100 Hz to 1 kHz in order to attenuate lower-frequency electrical signals that correspond to cardiac activity in the subject instead of the nerve activity. The lower-frequency cutoff of the high-pass filter can be adjusted based on the characteristics of different subjects to enable identification of the electrical signals in the nerves that innervate the skin while attenuating the electrical signals from muscles and other sources of electrical noise in the subject. For example, the high-pass filter may have a cutoff frequency of approximately 700 Hz. Thus, at process block 206, a skin activity may be identified using high-frequency signals that pass through the high-pass filter.

At process block 208, a sympathetic nerve activity may then be estimated using the identified skin nerve activity. For instance, predetermined correlations or relationships between skin nerve activity and a stellate ganglion nerve activity may be utilized to determine the estimates. Such correlations may be stored in a memory, for example. In this manner, an estimated sympathetic nerve activity may be provided in the form of a report at process block 210, enabling a clinician or other healthcare professional to monitor or assess nerve activity in the subject. The report may be provided in substantially real time, for example, using a display, or stored in a memory to be retrieved at a later time. In some aspects, the report may be in the form of graphs or time traces of measured or estimated nerve activity. Displayed or retrieved activities corresponding to estimated nerve activity may then utilized by a doctor or other healthcare professional during or following the course of medical treatment for a subject. The report may also include information derived from measurements or estimations of nerve activity, including average signals, signal variations, signal frequencies, frequency variations, identified events, event timings, deviations from a baseline, and so forth.

In one embodiment, the process 200 may be implemented in a passive operating mode, displaying the nerve activity and recording nerve activity in the memory for subsequent retrieval and analysis by medical professionals. In such passive operating mode, therapeutic devices need not be activated automatically. That is, a doctor or other healthcare provider would retrieve and review information or data associated with acquired or estimated nerve activity as part of diagnosis and treatment in a patient. The passive operating mode can be used, for example, during diagnosis of a medical condition, during long-term monitoring of a patient to assess progress in a course of medical treatment, and for studies of subjects during clinical trials or other scientific research.

In another embodiment, the process 200 may be carried out to generate a baseline measurement of nerve activity in a subject, such as stellate ganglion nerve activity baseline. For example, the baseline nerve activity can include an average signal amplitude, or signal variation. The baseline activity could then be used to determine a change in the level of nerve activity over time, for example, as a result of a change in medical condition, or as a result of treatment. A determined rapid change in the electrical signals corresponding to the sympathetic nerve activity that deviates from the baseline by more than a predetermined threshold, could then initiate an audio or visual alarm to a clinician in response to the identified change in nerve activity. In some aspects message, such as a page, email, or text message, through a data network may be sent to alert a remote healthcare professional of the identified event.

Figure 3:
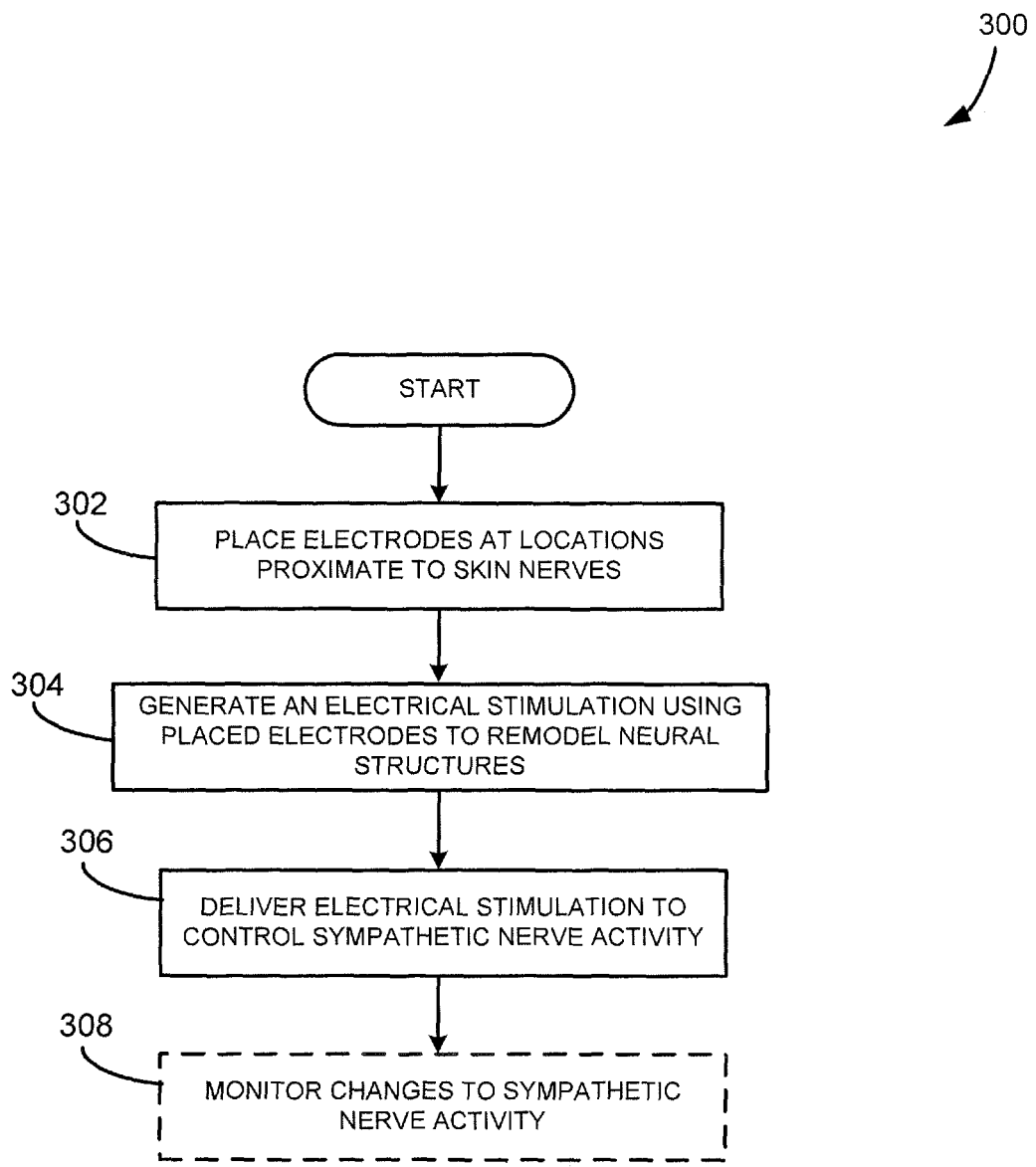
FIG. 3 shows steps of an example process for controlling nerve activity in a subject, in accordance with aspects of the present disclosure.

In accordance with another aspect of the present disclosure, FIG. 3 depicts steps of a process 300 for controlling nerve activity in a subject in accordance with aspects of the present disclosure. The process 300 may be carried out using a system 100 as described with reference to FIG. 1 or any other suitable system. In some aspects, the process 300 may be carried out as a result of a determined medical condition, or a deviation of nerve activity from a baseline.

Specifically, the process 300 may begin at process block 302 where subcutaneous and/or cutaneous electrodes may be placed at various locations proximate to nerves innervating a subjects skin. In some aspects, selection of electrode locations might take consideration of enervations proximate to the skin for the neural structure(s) targeted for control, in order to effectively deliver therapeutic effects. For example, electrodes may be placed at skin locations about the thorax of a subject, specifically at or above the $5^{th}$ thoracic space. In particular, this location is associated with connections between skin sympathetic nerves and the stellate ganglion. Other locations, depending upon the targeted neural structure, or tissue, may also be possible.

At process block 304, an electrical stimulation is then generated, for example, using system 100 as described. In accordance with aspects of the present disclosure, electrical stimulation parameters may configured to control a sympathetic nerve activity, such as a stellate ganglion nerve activity. In particular, the electrical stimulation may be configured to remodel one or more neural structures, such as the stellate ganglion. By way of example, an electrical stimulation treatment protocol may include an intermittent stimulation that includes short ON and long OFF periods. For instance, an ON time may be approximately 14 seconds in duration, while the OFF time may be approximately 1 minute to 3 minutes duration. The stimulation frequency may be approximately 10 Hz, with a pulse width of 0.5 milliseconds and an intensity amplitude in the range of 1.0 milliAmperes to 3.5 milliAmperes. In accordance with findings of the present disclosure, such mode of stimulation may be sufficient to control stellate ganglion nerve activity and maintain therapeutic effects. It may be appreciated that other electrical stimulations protocols may also be possible, depending upon targeted structures or tissues.

As indicated by process block 306, in order to control sympathetic nerve activity the electrical stimulation may be delivered via cutaneous and/or subcutaneous electrodes. In some applications, stimulation output may be adjusted gradually over a period of time. For example, the stimulation may be adjusted over 3 weeks, from 0.5 milliAmperes to 3.5 milliAmperes, and maintained in accordance with target remodeling or nerve activities.

In some aspects, changes to a sympathetic nerve activity, such as the stellate ganglion nerve activity may also be monitored at process block 308. For instance, a sympathetic nerve activity may be estimated using measures of skin nerve activity, as described, via electrical signals acquired from locations proximate to a subject's skin. A report may also be generated at process block 308, including information associated with the administered electrical stimulations, as well as any changes to sympathetic nerved activities detected.

Figure 4:
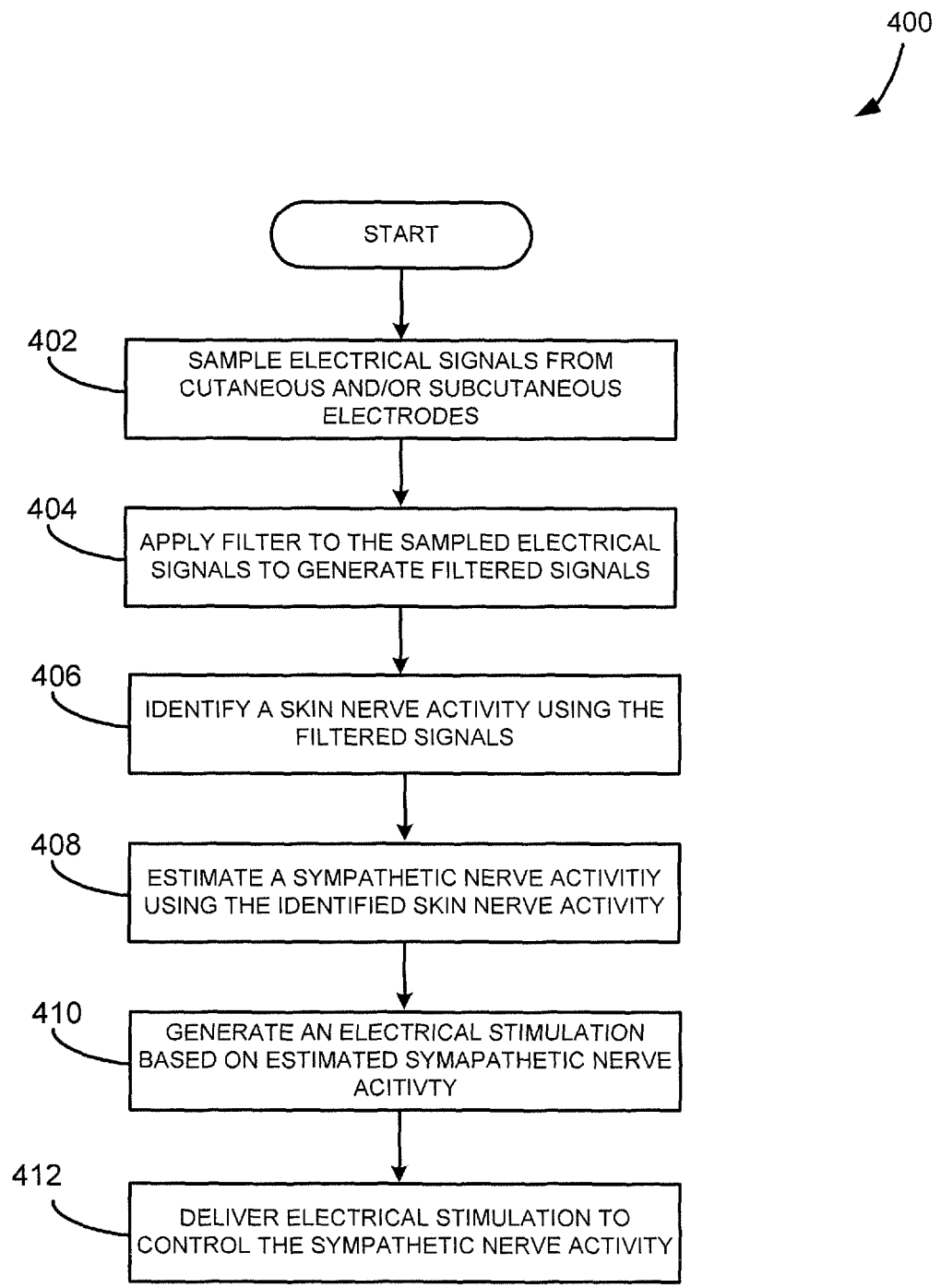
FIG. 4 shows steps of another example process for controlling nerve activity in a subject, in accordance with aspects of the present disclosure.

In accordance with yet another aspect of the present disclosure, FIG. 4 depicts steps of a process 400 for controlling nerve activity in a subject using cutaneous and/or subcutaneous electrodes that deliver electrical stimulations via nerves that innervate the skin. The process 400 may be carried out using a system 100 as described with reference to FIG. 1 or any other suitable system.

Similar to process 200 depicted in FIG. 2, a sympathetic nerve activity may be estimated using skin measures. Specifically, in some aspects, electrical signals originating from cutaneous and/or subcutaneous electrodes (block 402) may be amplified, sampled and filtered (block 404). In some aspects, the applied filter may be configured to attenuate at least signals having frequencies that correspond to heart muscle activity during a heartbeat. Using identified skin nerve activity (block 406) generated using filtered electrical signals, an estimate of sympathetic nerve activity may then be obtained using correlations stored in a memory, for example, as indicated by process block 408. In some aspects, various computations may be also carried out at process block 408 using the estimated sympathetic nerve activity, including computing average signals, signal variations, signal frequencies, frequency variations. In some aspects, certain events, event timings, deviations from a baseline, and other information may also be obtained at process block 408.

Then, at process block 410, and electrical stimulation based on the estimated sympathetic nerve activity, and or information obtained therefrom, may be generated, and subsequently delivered at process block 412. In some aspects, delivered electrical stimulations may be used control the sympathetic nerve activity, for example, by remodeling one or more neural structures. In addition, nerve activity following delivery of the electrical stimulation may also be monitored at process block 412, as described.

The above-described system and methods may be further understood by way of examples. These examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, certain electrode arrangements and configurations are presented, although it may be understood that other configurations may be possible, and still considered to be well within the scope of the present invention. Likewise, specific process parameters and methods are recited that may be altered or varied based on variables such as signal amplitude, phase, frequency, duration, and so forth.

Example I

Previous studies have documented a direct relationship between stellate ganglion nerve activity ("SGNA") and cardiac arrhythmias in ambulatory dogs. In addition to serving as a source of cardiac sympathetic innervation, the stellate ganglia also gives rise to sympathetic nerves that innervate blood vessels and sweat glands in skin. It was shown recently that it is feasible to record sub-cutaneous nerve activity ("SCNA") from ambulatory dogs continuously over long periods of time, and that the SCNA can be used to estimate the cardiac sympathetic tone. The latter observations are extended in the present study by documenting the feasibility of directly recording sympathetic nerve activities from the skin of the chest. Specifically, the present study was aimed at testing the hypothesis that thoracic skin nerve activity ("SKNA") can be used to estimate SGNA in both anesthetized and ambulatory dogs. A method was developed for recording skin nerve activity, and a comparison was made between SKNA, SGNA and heart rate.

Figure 5:
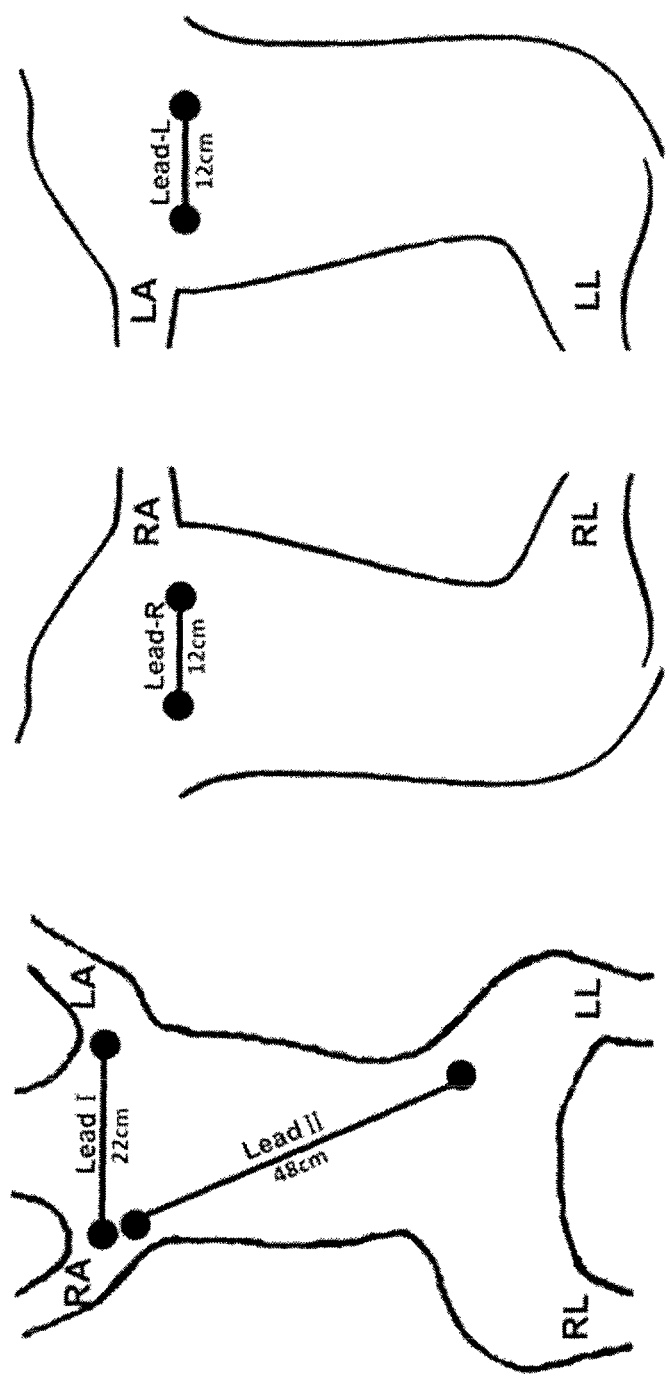
FIG. 5 is a schematic showing an example electrode lead configurations on the surface of an animal subject's skin.

In a first protocol, Protocol 1, five anesthetized dogs (A, B, C, D, E) were used to assess Right SGNA and SKNA. The first two dogs were also used for subcutaneous nerve activity ("SCNA") recording. The dogs were intubated and underwent isoflurane general anesthesia. Thoracotomy was performed through the right 3rd intercostal space and the hair on the thoracic skin was removed. A pair of bipolar electrodes was inserted under the fascia of the right stellate ganglion. Electrocardiogram ("ECG") patches (Tyco/Healthcare Kendall, Medi-Trace 100, Hampshire, U.K.) were secured on the skin using adhesive tapes for surface ECG and SKNA recording. Two pairs of those ECG patch electrodes were taped on the skin to record ECG Leads I and II, along with SKNA. As shown in FIG. 5, Lead I was recorded between electrodes at the level of the $2^{nd}$ rib with an inter-electrode distance of 22 cm. Lead II was recorded between electrodes on right second rib and the left lower abdomen, with an inter-electrode distance of 48 cm. An additional patch was secured to the right lower abdomen to serve as ground.

To explore whether or not other locations on the chest wall can also be used for SKNA recording, a pair of bipolar electrodes was placed each at the level of the right and left $3^{rd}$ rib in dogs B and C, respectively, to form bipolar electrodes with 12 cm inter-electrode distance (FIG. 5). In dogs D and E, these bipolar electrodes were moved downwards to the lower ⅓rd of the chest to determine if SKNA from the lower chest can also be used for recording cardiac sympathetic tone.

These electrodes were connected to a World Precision Instrument Iso-Damm-8 amplifier (Sarasota, Fla.), with a noise level of <±2.5 μV and a recording bandwidth set at 10 Hz-3 KHz. The signals were digitized by Digidata 1400a using AxoScope software (Sunnyvale, Calif.) at 10,000 times per second per channel. After all surgical procedures were performed, the anesthetic agents were switched from isoflurane to alpha-chloralose (up to 100 mg/kg) and morphine. One ml apamin (concentration 0.2 ng/μL) was injected directly into the right stellate ganglion, which is a neurotoxin that is a specific blocker of the small conductance calcium activated K (SK) channel. Inhibition of the SK channel is known to facilitate neuronal discharges. Data was acquired for 10 min after apamin injection.

In a second protocol, Protocol 2, four ambulatory dogs (F, G, H, I) were used to assess Left SGNA and SKNA. All four dogs were chronically instrumented for different research protocols. However, the non-invasive recordings made in this study did not affect the results of those research protocols, and only helped reduce the use of animals.

The dogs underwent left thoracotomy through the third intercostal space. A DSI (Data Sciences International, St. Paul, Minn.) D70EEE radiotransmitter was implanted to record the left SGNA and the subcutaneous ECG according to methods reported elsewhere. Dogs F and G were normal dogs and did not undergo other procedures. Dog H had undergone left circumflex coronary artery ligation to create myocardial infarction. Dog I had undergone a modified Secura implantable cardioverter-defibrillator (Medtronic, Minneapolis, Minn.) implantation for intermittent rapid left atrial pacing in an attempt to induce paroxysmal AF. That dog was in sinus rhythm when used in this study. All dogs were allowed to recover for 2 weeks after the initial surgery.

At the time of the study, all wounds have healed and the dogs were ambulatory. After clipping the hair on the chest, four ECG patches were placed on the skin to record surface ECG Leads I and II according to the methods described in Protocol 1. An additional two pairs of bipolar electrodes were placed on the upper $\frac{1}{3}^{rd}$ of the skin of the left and right thorax for bipolar ECG recordings. Soft, non-adhesive elastic bands were used to wrap around the chest to help secure the ECG patches in place. The locations of surface ECG patch electrodes were the same as shown in FIG. 5. These skin electrodes were connected to the same equipment as described in Protocol 1. Continuous recordings were made for 30 min while the dog was awake and lying or standing in the dog run.

Recordings were analyzed using custom written DSIView software. The same ECG signals were used for both SKNA and ECG analyses. The signals were high-pass filtered at 700 Hz to display SKNA and low pass filtered at 30 Hz to display the surface ECG. The latter was used for heart rate analyses. A quantitative analyses was performed by integrating SGNA (iSGNA), SKNA (iSKNA) minute by minute. The data was reported in the form of a mean and 95% confidence interval (CI). Pearson correlation coefficients were calculated between heart rate, iSGNA and iSKNA. A p value of ≤0.05 was considered statistically significant Results Protocol 1: Correlation Between iSGNA and iSKNA after Apamin Injection grated right SGNA ("iRSGNA"), integrated SKNA recorded by ECG Lead I ("iSKNA-I"), ECG Lead II ("iSKNA-II"), right chest ("iSKNA-R"), left chest ("iSKNA-L") and heart rate ("HR") of the same dog. All of them strongly correlated with each other.

Figure 7A:
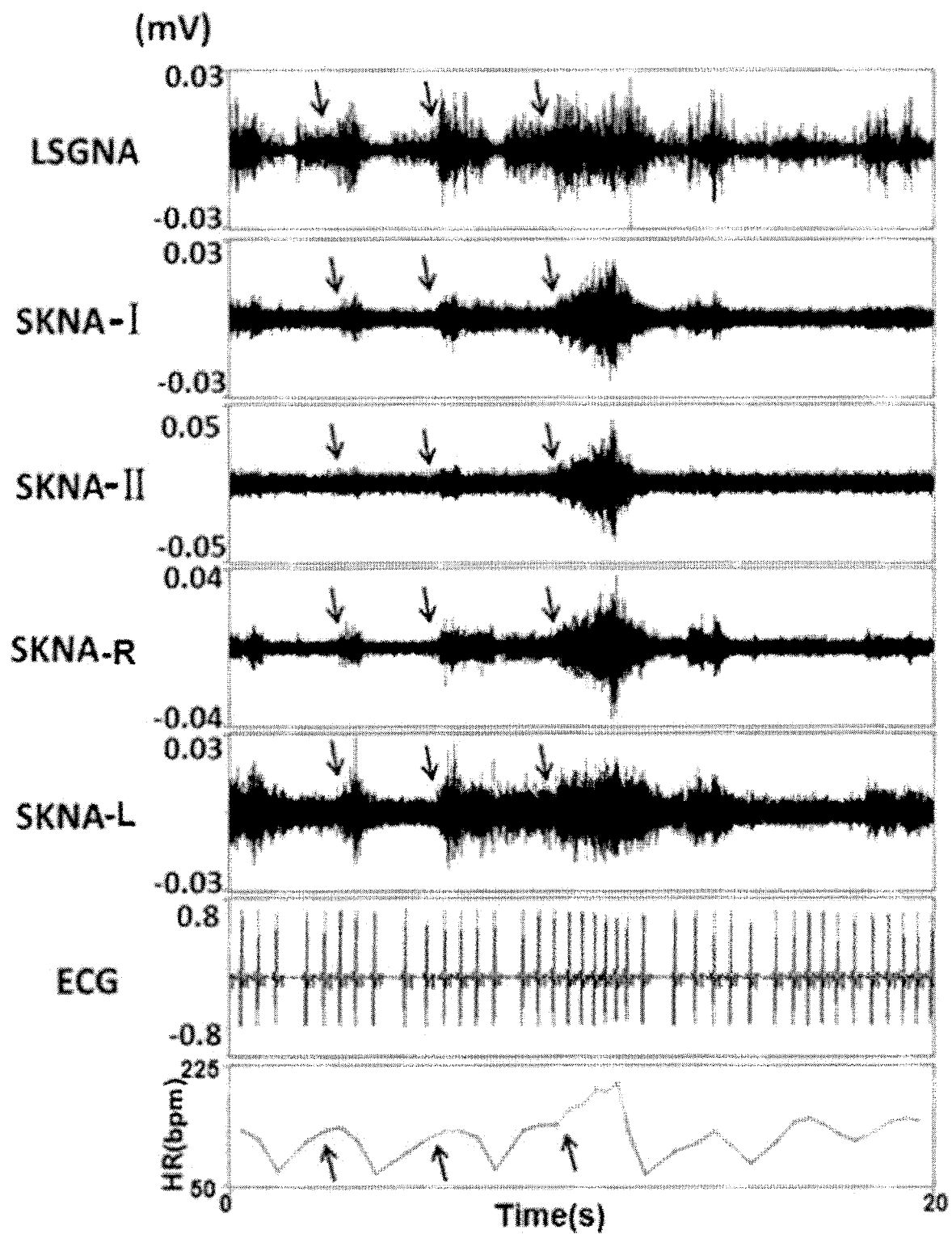
FIG. 7A shows example time traces illustrating spontaneous correlated events associated with stellate ganglion activity, skin nerve activity, cardiac activity and heart rate in an animal subject.
Figure 7B:
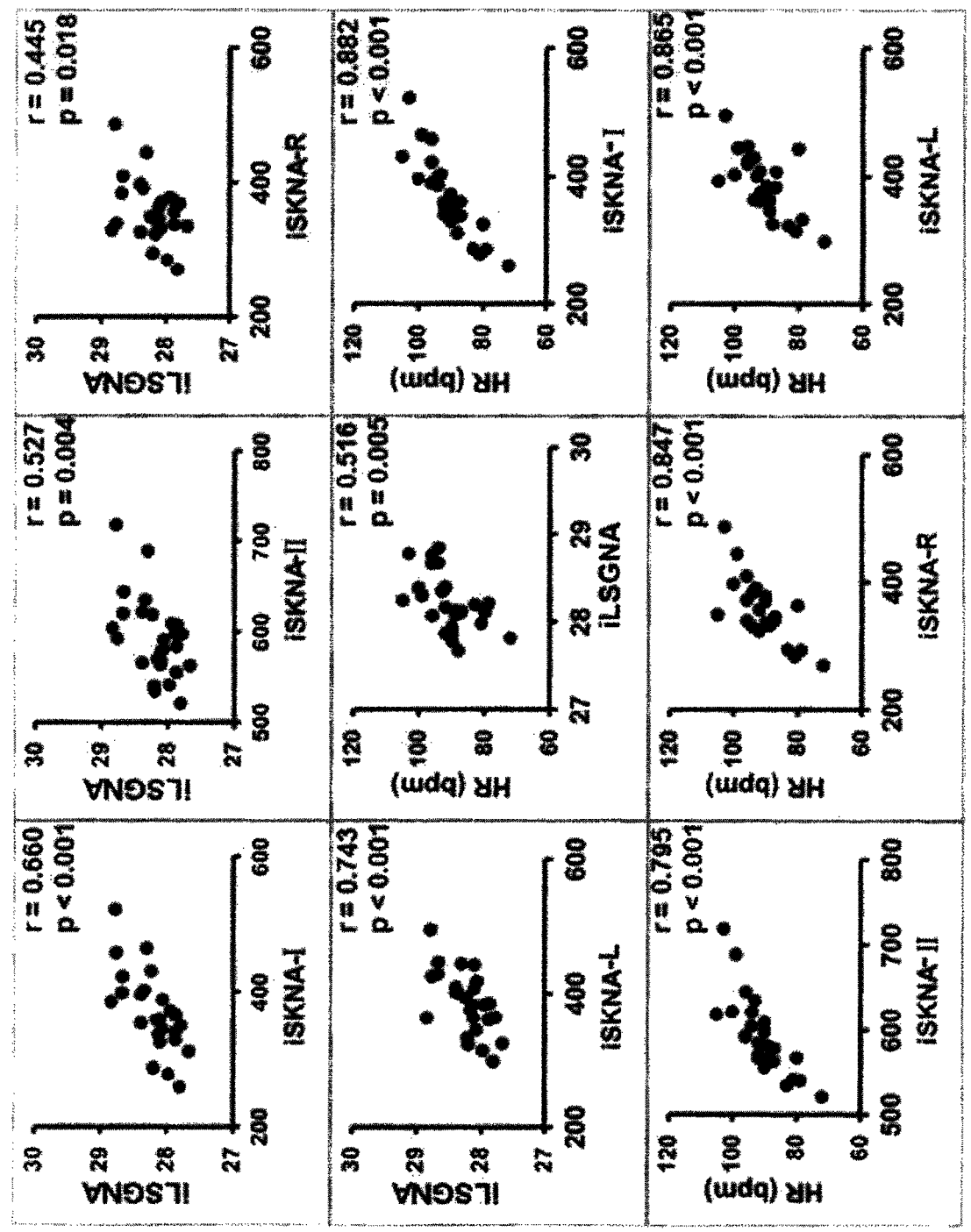
FIG. 7B shows graphs indicating correlations between stellate ganglion activity, skin nerve activity and heart rate in an ambulatory animal subject.

Protocol 2: Monitoring of Spontaneous SKNAs and SGNA, Heart Rate in Ambulatory Dogs Simultaneous recording of SGNA and SKNAs was successful in all dogs studied. There were electrical signals resembling nerve activities on the surface of skin. During the recording period, the sound created by the investigators (speaking, clapping of the hands, moving instruments around) or barking of other dogs in the same room often caused abrupt activation of the SGNA. FIG. 7 shows correlations between left stellate ganglion activity ("LSGNA"), cardiac activity and skin nerve activity ("SKNA") in an ambulatory dog. Specifically, FIG. 7A shows nerve activities (high pass filtered at 700 Hz) recorded both from LSG and from all skin electrodes from dog I. The SGNA was associated with elevated heart rate and the SKNA at all locations. The third arrow shows that largest heart rate acceleration associated with largest LSGNA and SKNA recordings. A large nerve activity ((downward arrows) is associated with large increase in heart rate ("HR") (upward arrow). FIG. 7B shows the correlation between integrated nerve activities and average heart rates, with each dot representing data collected in a one-min window. There are significant correlations for all comparisons in this dog. Specifically, significantly positive correlations are shown among integrated left SGNA (iLSGNA) and iSKNA-I, iSKNA-II, iSKNA-R, iSKNA-L and heart rate.

TABLE 1

Correlation Coefficients Between Nerve Activities and Heart Rate for Each Dog.

| Dog # | iRSGNA vs. iSKNA-I | iRSGNA vs. iSKNA-II | iRSGNA vs. iSKNA-R | iRSGNA vs. iSKNA-L | HR vs. iRSGNA | HR vs. iSKNA-I | HR vs. iSKNA-II | HR vs. iSKNA-R | HR vs. iSKNA-L |
|---|---|---|---|---|---|---|---|---|---|
| Protocol 1. | | | | | | | | | |
| A | r = 0.948 | 0.933 | — | — | 0.834 | 0.886 | 0.859 | — | — |
|   | p < 0.001 | <0.001 | | | 0.005 | 0.001 | 0.003 | | |
| B | r = 0.749 | 0.729 | 0.864 | 0.715 | 0.875 | 0.823 | 0.907 | 0.725 | 0.586 |
|   | p = 0.020 | 0.026 | 0.003 | 0.031 | 0.002 | 0.006 | 0.001 | 0.027 | 0.097 |
| C | r = 0.985 | 0.881 | 0.951 | 0.885 | 0.867 | 0.783 | 0.933 | 0.600 | 0.583 |
|   | p < 0.001 | 0.002 | <0.001 | 0.002 | 0.002 | 0.013 | <0.001 | 0.088 | 0.099 |
| D | r = 0.950 | 0.773 | 0.748 | 0.564 | 0.926 | 0.929 | 0.715 | 0.551 | 0.539 |
|   | p < 0.001 | 0.014 | 0.020 | 0.114 | <0.001 | <0.001 | 0.030 | 0.125 | 0.135 |
| E | r = 0.751 | 0.603 | 0.802 | 0.772 | 0.881 | 0.766 | 0.548 | 0.453 | 0.507 |
|   | p = 0.020 | 0.086 | 0.009 | 0.015 | 0.002 | 0.016 | 0.126 | 0.221 | 0.163 |
| Mean | 0.877 | 0.784 | 0.841 | 0.734 | 0.877 | 0.837 | 0.792 | 0.582 | 0.554 |
| Protocol 2 | | | | | | | | | |
| F | r = 0.745 | 0.601 | 0.575 | 0.678 | 0.620 | 0.824 | 0.335 | 0.319 | 0.811 |
|   | p < 0.001 | 0.005 | 0.001 | <0.001 | 0.004 | <0.001 | 0.149 | 0.098 | <0.001 |
| G | r = 0.624 | 0.464 | 0.444 | 0.529 | 0.649 | 0.525 | 0.377 | 0.170 | 0.591 |
|   | p = 0.001 | 0.026 | 0.038 | 0.011 | 0.001 | 0.010 | 0.076 | 0.449 | 0.004 |
| H | r = 0.539 | 0.547 | 0.350 | 0.719 | 0.790 | 0.722 | 0.582 | 0.631 | 0.499 |
|   | p = 0.025 | 0.023 | 0.142 | 0.001 | <0.001 | 0.001 | 0.014 | 0.004 | 0.030 |
| I | r = 0.660 | 0.527 | 0.445 | 0.743 | 0.516 | 0.882 | 0.795 | 0.847 | 0.865 |
|   | p < 0.001 | 0.004 | 0.018 | <0.001 | 0.005 | <0.001 | <0.001 | <0.001 | <0.001 |
| Mean | 0.642 | 0.535 | 0.454 | 0.667 | 0.644 | 0.738 | 0.522 | 0.492 | 0.692 |

Figure 6A:
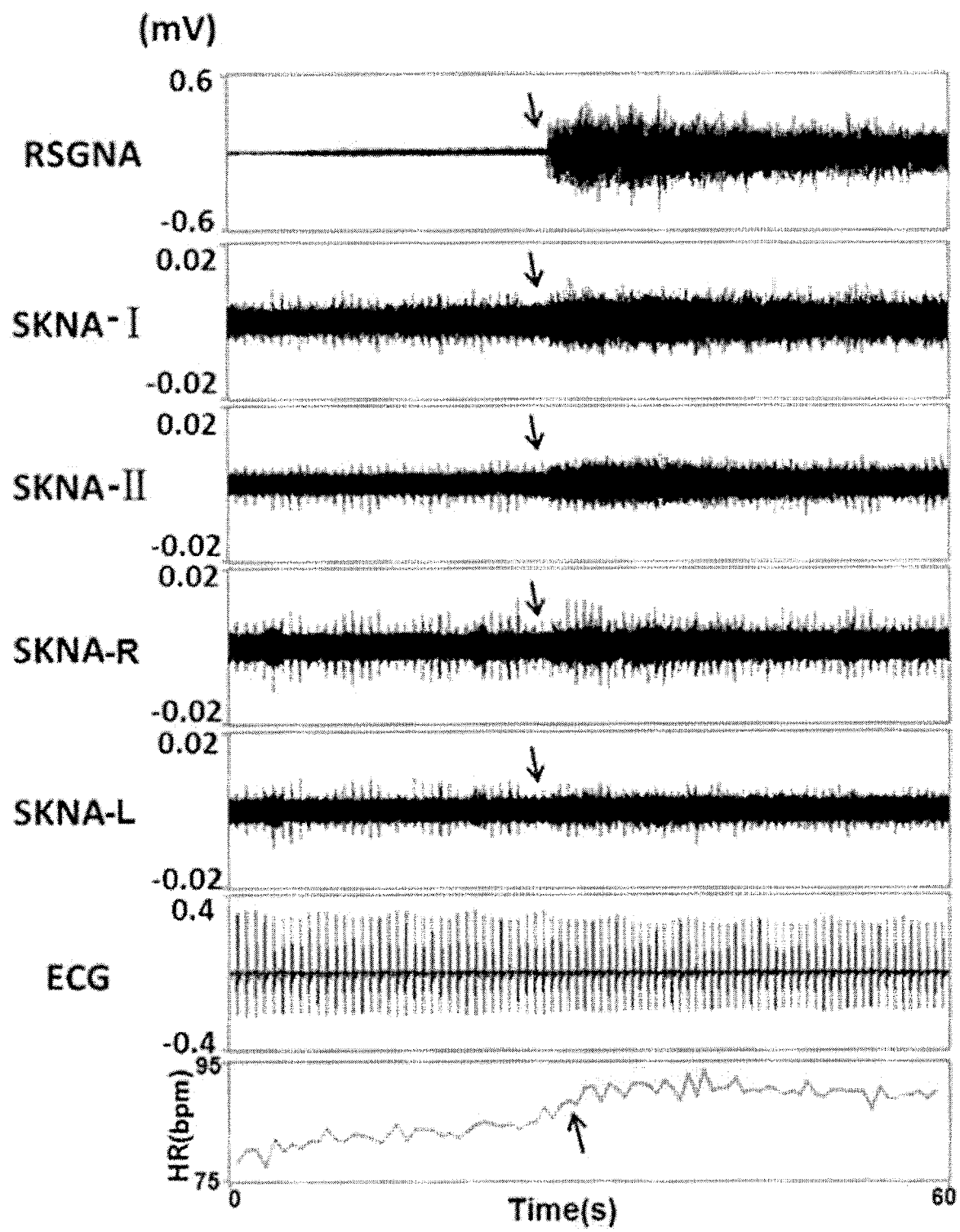
FIG. 6A shows example time traces of stellate ganglion activity, skin nerve activity, cardiac activity and heart rate before and after administration of apamin.
Figure 6B:
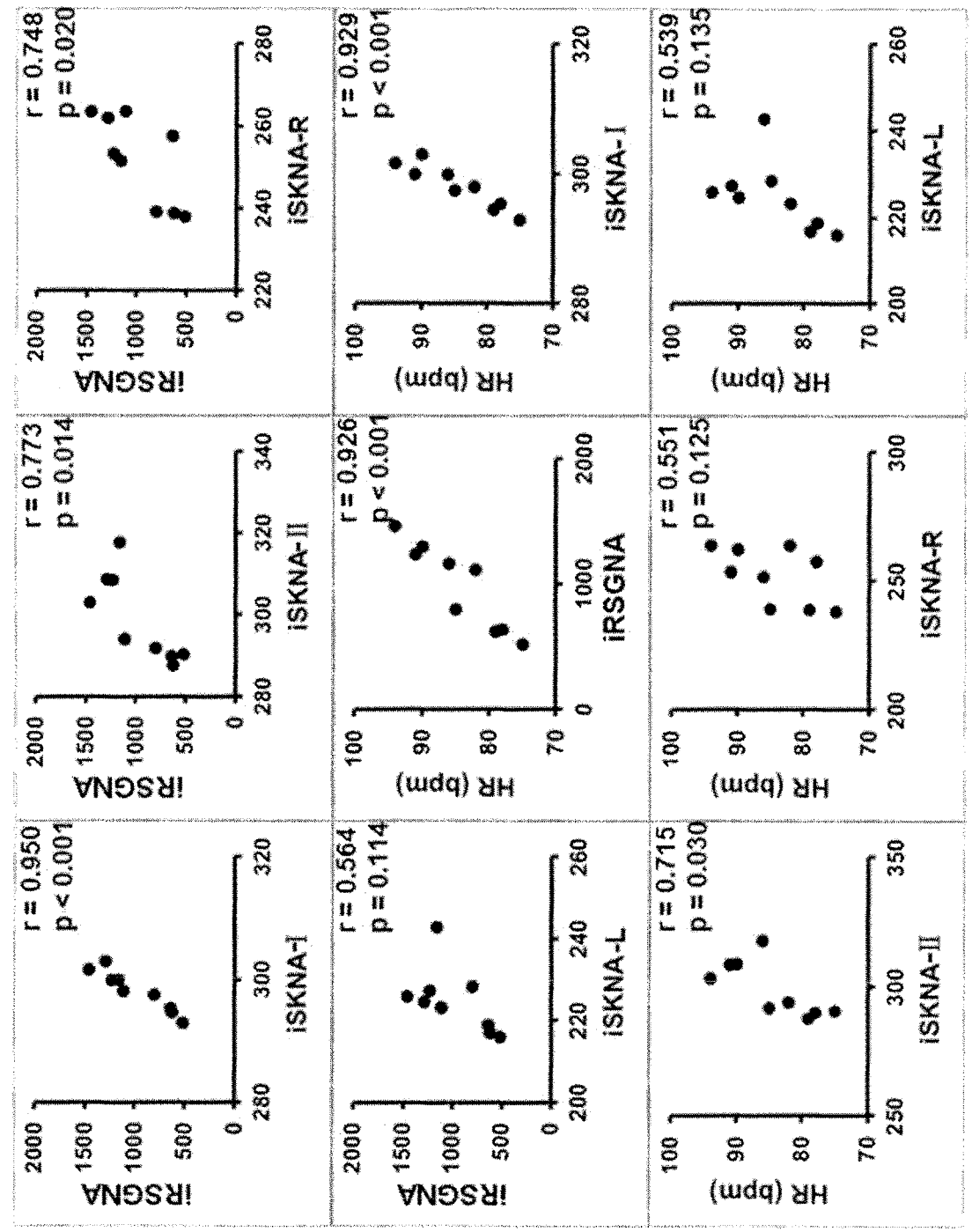
FIG. 6B shows graphs indicating correlations between stellate ganglion activity, cardiac activity and skin nerve activity for an animal subject

Apamin injection induced robust activity of SKNA and SGNA in all dogs studied. FIG. 6A shows a typical recording from Dog D. Apamin-induced SGNA, SKNA and heart rate acceleration. FIG. 6B shows the relationship among inte- Table 1 shows the correlation coefficient and the p values of all dogs studied. As shown in this table, there is consistently a strong positive correlation (mean 0.877) found between iSGNA and iSKNA-I in all dogs of Protocol 1. A good correlation (mean 0.642) was found between iSGNA and iSKNA-I in Protocol 2. Both right and left integrated SGNA (iRSGNA and iLSGNA) correlated well with the ipsilateral integrated SKNA (iRSKNA and iLSKNA) respectively. All other correlations are positive and mostly statistically significant.

Simultaneous recording of SGNA and SKNAs was successful in all dogs studied. There were electrical signals resembling nerve activities on the surface of skin. During the recording period, the sound created by the investigators (speaking, clapping of the hands, moving instruments around) or barking of other dogs in the same room often caused abrupt activation of the SGNA. FIG. 7A shows a typical recording from dog I. The SGNA was associated with elevated heart rate and the SKNA at all locations. The third arrow shows that largest heart rate acceleration associated with largest LSGNA and SKNA recordings. FIG. 7B shows significantly positive correlations among integrated left SGNA ("iLSGNA") and iSKNA-I, iSKNA-II, iSKNA-R, iSKNA-L and heart rate.

Results from this study demonstrated that (1) it is feasible to record sympathetic nerve activities from the surface of skin and (2) there was a positive and statistically significant positive correlation between iSGNA with iSKNA-I, and between iSGNA and the ipsilateral iSKNA. These findings indicate that SKNA recorded from the Lead I ECG and from ipsilateral bipolar surface ECG leads can be used to estimate the SGNA and cardiac sympathetic tone.

In the present study, four pairs of bipolar electrodes (leads I, II, right and left) were implanted on the surface of the skin to record SKNAs. All dogs (9/9) showed a significant correlation between iSKNA-I and iRSGNA or iLSGNA. Eight (8/9) dogs showed a strong correlation between iSKNA-II and iRSGNA or iLSGNA. Seven (7/8) dogs showed a good correlation between iSKNA-R or iSKNA-L and iRSGNA or iLSGNA. In addition, all dogs (9/9) showed a significant correlation between iSKNA-I and heart rate. Six dogs (6/9) showed a strong correlation between iSKNA-II and heart rate. Three (3/8) dogs showed a good correlation between iSKNA-R and heart rate and four (4/8) dogs showed a good correlation between iSKNA-L and heart rate. Therefore, SKNA-I may be the best recording lead to estimate the SGNA and the cardiac sympathetic tone. In addition, a good correlation between iSGNA and ipsilateral iSKNA is compatible with the finding that the skin sympathetic innervation came from ipsilateral stellate ganglion. However, because the left and right stellate ganglion usually fire simultaneously, the integrated SKNA recorded from any location on the chest correlated positively with both right and left SGNA.

The correlations between SGNA and SKNA for all combinations appear to be stronger in Protocol 1 than Protocol 2. A possible explanation may be that the equipment used to record SGNA in Protocol 1 had much higher frequency bandwidth than that used in Protocol 2. The latter study used implanted DSI radiotransmitter which are adequate in recording the large nerve discharges associated with the abrupt onset of sinus tachycardia, but often misses the smaller changes of nerve discharges associated with transient shortening of RR interval. The weaker correlation is likely the result of insufficient frequency content of the SGNA recording.

SKNA may be useful clinically for cardiac arrhythmia risk stratification. It may also be helpful in determining the relationship between sympathetic tone and cardiac arrhythmia in animal models without a need for thoracotomy. Results here also show that it is possible to simultaneously record the ECG and SKNA from the surface of thoracic skin using the same pair of ECG patch electrodes. The same signals are low-pass filtered for selective ECG signals and high-pass filtered for SKNA signals. The latter techniques may be useful in clinical investigations for a better understanding of the relationship between sympathetic nerve activities and cardiac arrhythmogenesis.

Example II

Histological studies of human skin biopsy have confirmed the presence of abundant sympathetic nerves in arteriovenous anastomoses, arrector pilorum muscles, and arterioles. Using horseradish peroxidase as tracer, one group found that all skin sensory and sympathetic neurons are located ipsilaterally. Nearly all sympathetic somata are located in the middle cervical and stellate ganglia. Because of the direct and extensive connections among various nerve structures, it is possible for the sympathetic nerves in the various structures to activate simultaneously. Using bipolar electrodes located in the chest wall, the present study aimed to obtain good ECG signals for heart rate analyses as well as record nerve signals over a wide area in the left lateral thorax. The onset and offset of nerve activities in the thoracic subcutaneous space and the stellate ganglion were documented simultaneously or nearly simultaneously, showing that nerve activities correlate with the heart rate. These observations made it possible to directly assess cardiac sympathetic tone by electrodes embedded in the thoracic subcutaneous space of ambulatory dogs.

Two acute and three chronic canine experiments were performed to test the hypothesis that cutaneous or subcutaneous stimulation can remodel the stellate ganglion, and modify SGNA. Previous studies showed that acupoint is richly innervated by autonomic nerve fibers. Therefore, subcutaneous tissues near the Xinshu acupoint of the dogs were explored for sympathetic nerves. The Xinshu acute point is located on the back, below the spinous process of the 5th thoracic vertebra, 1.5 cun (roughly 5.5 cm) lateral to the posterior midline. (one cun, or Chinese inch, is roughly 3.715 cm in length.) That area was explored in dogs and small strands of subcutaneous nerves running through that region were identified.

Figure 8:
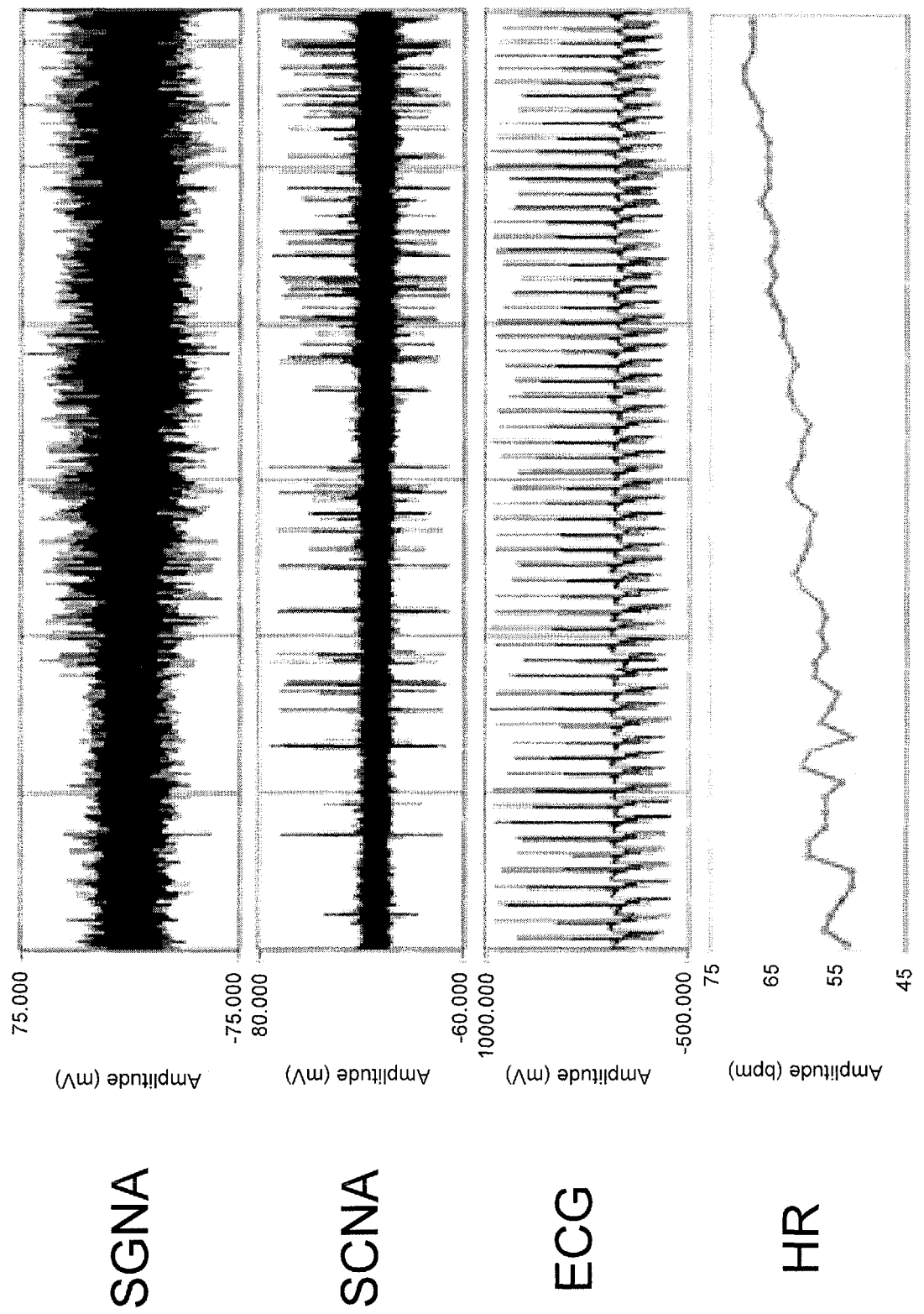
FIG. 8 is a graphical illustration showing increased subcutaneous nerve activity followed by increased stellate ganglion activity and heart rate following administration of apamin.

In the acute study, apamin (a neural toxin that increases nerve discharges) was injected into that subcutaneous nerves identified at the left Xinshu acupoint. It was found that the injection induced increased subcutaneous nerve activity ("SCNA") followed by increased left SGNA (FIG. 8). These experiments indicate that activation of the subcutaneous nerves can lead to subsequent activation of the left stellate ganglion in approximately 2-3 minutes. There was heart rate elevation associated with the increased nerve activity, confirming the physiological connection. The heart rate correlated well with the integrated SGNA ($r=0.86$) and with the integrated subcutaneous nerve activity (SCNA, $r=0.77$) after apamin injection.

Figure 9:
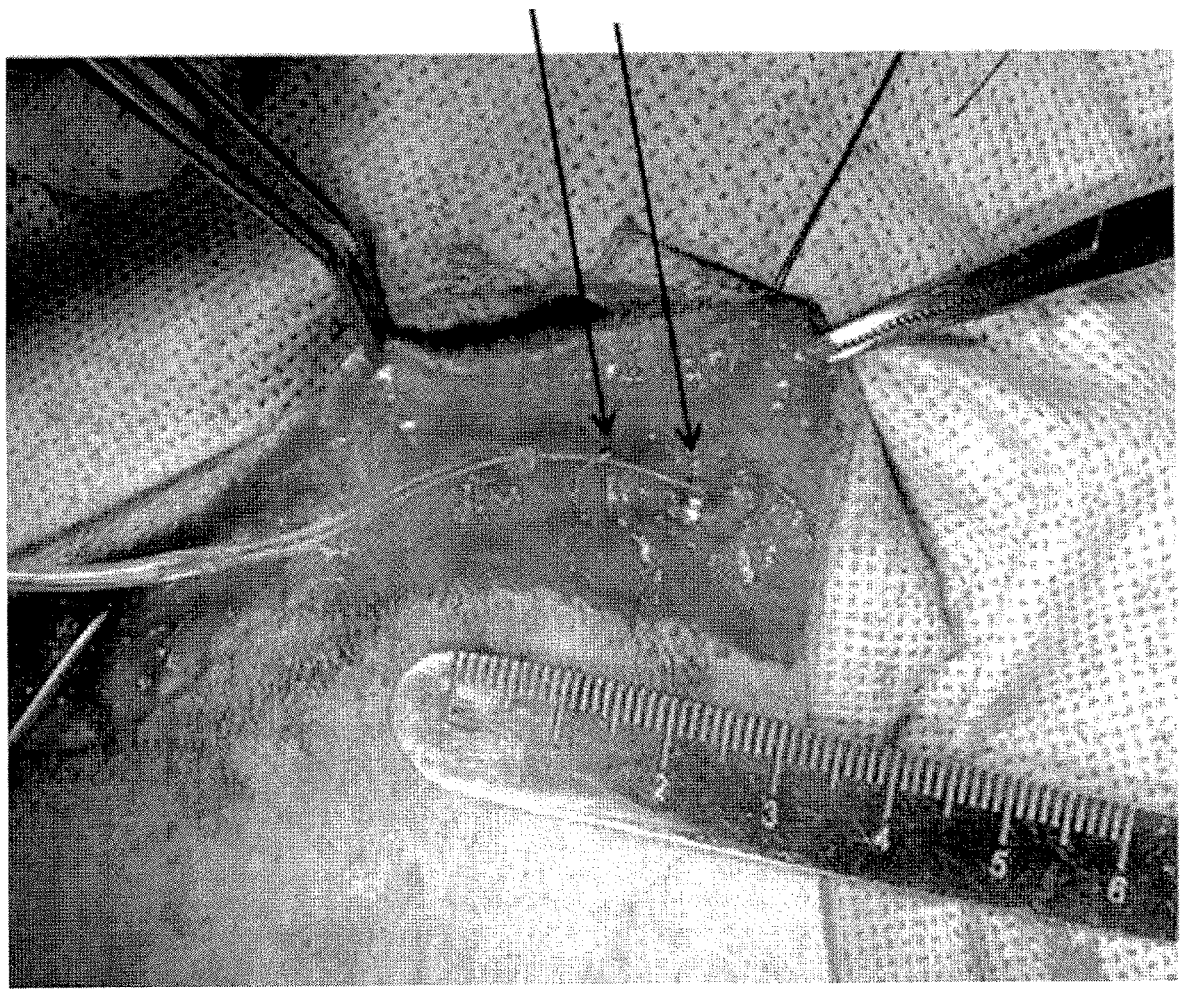
FIG. 9 is an image showing placement of subcutaneous stimulation wires in the Xinshu acupoint of an animal subject.

If the stellate ganglion can be acutely activated, then chronic activation of the stellate ganglion may cause remodeling changes of the left stellate ganglion. Therefore, instead of using apamin, electrical stimulations were used to activate the electrodes and achieve therapeutic effects. Specifically, stimulating electrodes were placed at locations associated with subcutaneous nerves of the animal subject, and the animal was allowed to recover from surgery. FIG. 9 shows a picture of the implanted electrodes in the present canine study. The nerve stimulation was given by a Cyberonics Demipulse vagal nerve stimulator. Instead of having electrodes wrapping around the vagal nerve, electrodes shown in FIG. 9 are wrapped around small subcutaneous nerves. The results of the acute (non-survival) study showed similar effects as the apamin injection, i.e., stimulating the subcutaneous nerve at Xinshu acupoint can activate the left stellate ganglion.

Recordings of subcutaneous electrodes were used to observe the effects of stimulation in chronically instrumented ambulatory dogs. For chronic studies of nerve recordings, an implanted Data Sciences International ("DSI") D70EEE radiotransmitter was utilized along with a Cyberonics Demipulse generator to deliver sub-cutaneous nerve stimulation and obtain the data. The stimulation protocol utilized was as follows: 0.5 mA for 2 days, 1.0 mA for 2 days, 1.5 mA for 2 days, 2.5 mA for 3 days and 3.5 mA for 2 weeks.

Figure 10:
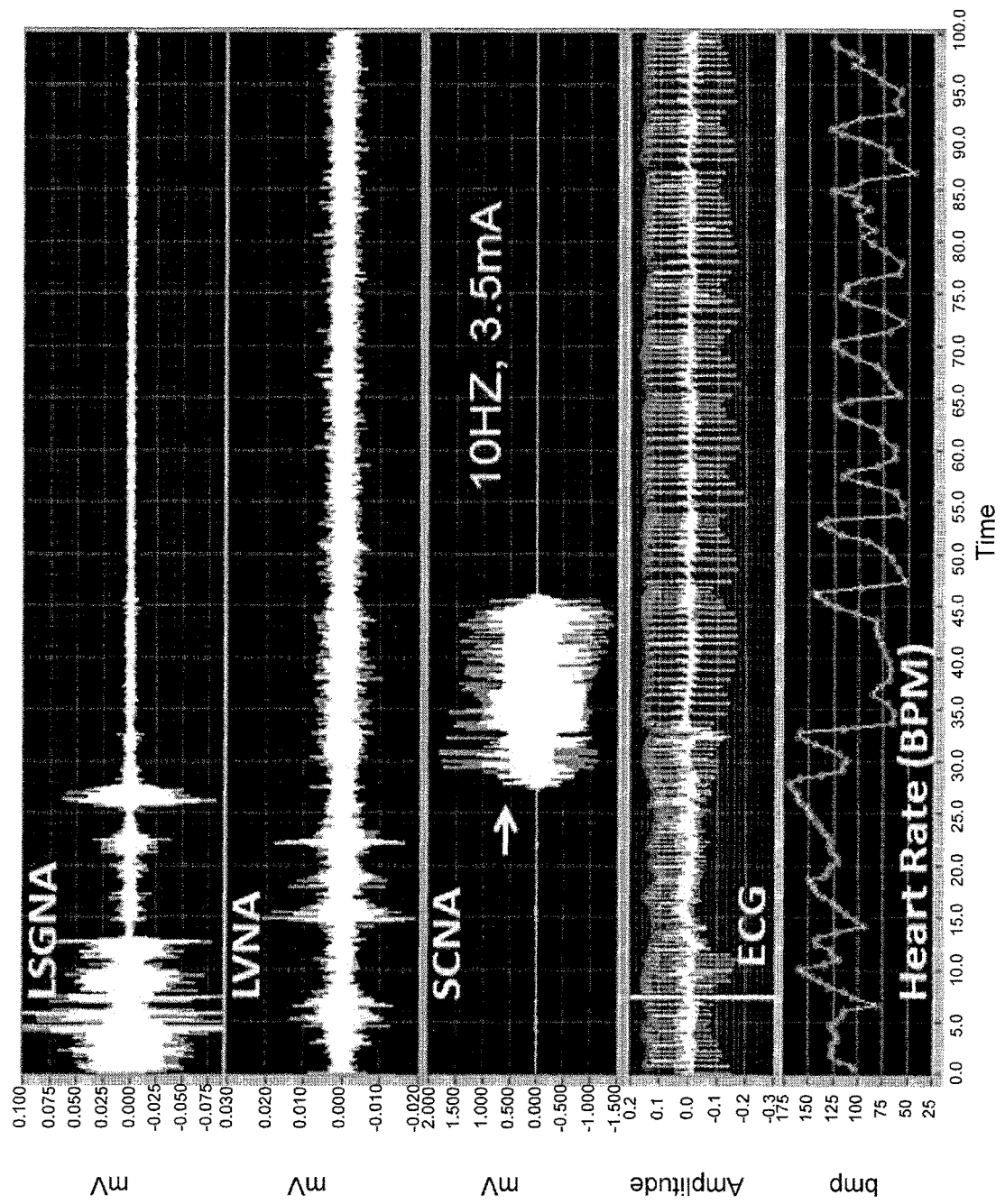
FIG. 10 shows example time traces of different nerve activities before and after subcutaneous nerve stimulation, in accordance with aspects of the present disclosure.

FIG. 10 shows the simultaneous recording of SGNA, left thoracic vagal nerve activity ("VNA") and the subcutaneous nerve activity (SCNA) in an ambulatory dog. The stimulation was given at 10 Hz, 14-s duration and 3.5 mA amplitude. The total duration of stimulation exceeded two weeks. The SCNA appears saturated with the stimulus artifact during the time of stimulation. As shown, there was activation of VNA and reduction of SGNA during the stimulation, indicating direct effects of the subcutaneous stimulation on the SGNA and VNA. Contrary to what was observed during acute study, the dogs with prolonged periods (weeks) of chronic subcutaneous nerve stimulation were associated with reduced overall SGNA.

Figure 11:
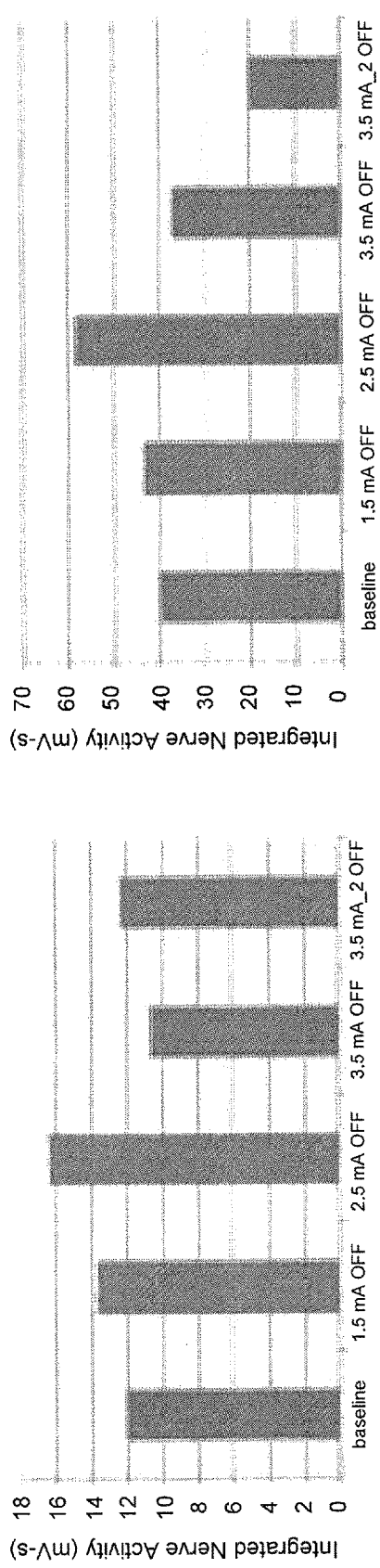
FIG. 11 are graphs showing effects on subcutaneous nerve activity, stellate ganglion nerve activity, heart rate, and vagal nerve activity following subcutaneous nerve stimulation.
Figure 11:
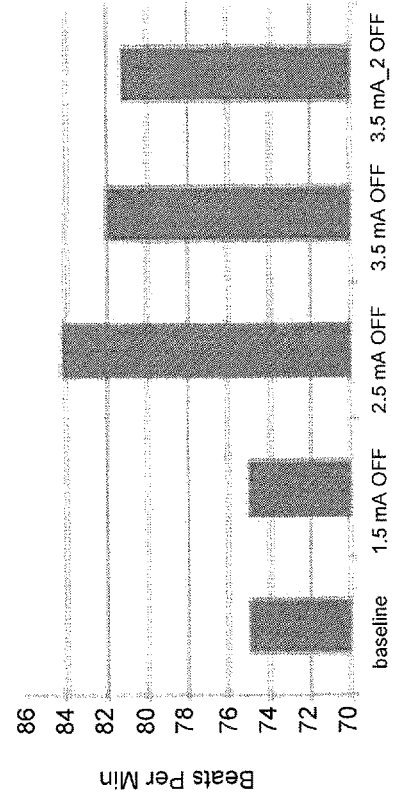

A quantitative analyses was performed on the nerve activities and heart rate in dogs with chronic subcutaneous nerve stimulation, with results shown in FIG. 11. Specifically the effects of subcutaneous stimulation during the OFF time are compared to baseline values for subcutaneous nerve activity, stellate ganglion nerve activity, heart rate and vagal nerve activity. Of note is that there is significant reduction of stellate ganglion nerve activity with 3.5 mA of intermittent stimulation, as compared to baseline. These findings are similar to observations in dogs following vagal nerve stimulation, highlighting the feasibility of subcutaneous stimulation.

In addition, subjects were then sacrificed and the left stellate ganglion was fixed with 4% of formalin for 45 min, followed by storage in 75% alcohol. The tissue samples of the left stellate ganglion were then paraffin embedded and cut into 5 µm thick sections. An immunohistochemical staining of tyrosine hydroxylase ("TH") using monoclonal anti-TH antibody (Accurate Chemical, Westbury, N.Y.) was then performed.

Figure 12A:
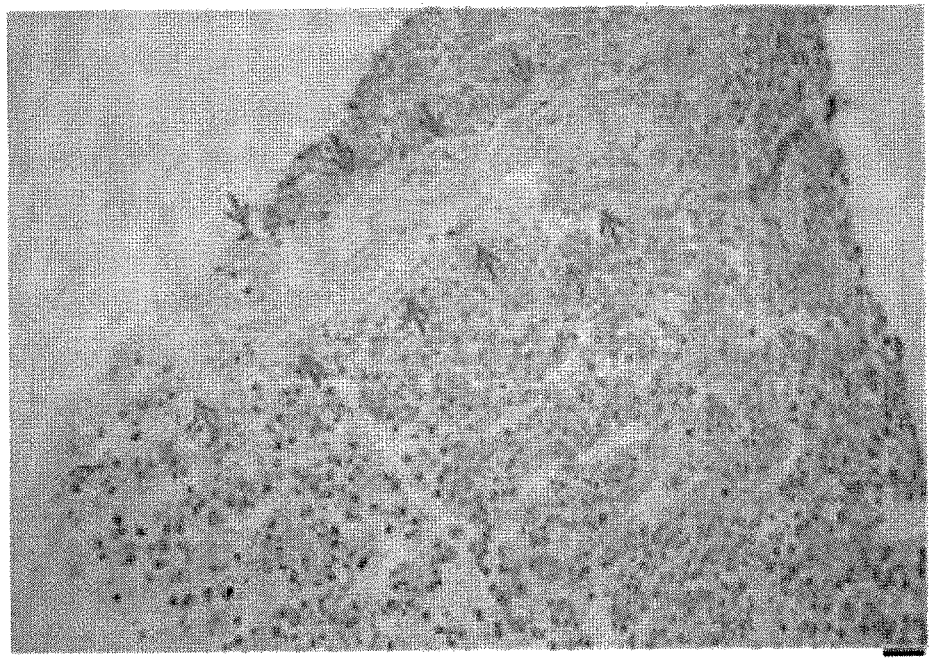
FIG. 12A is an image of a tyrosine hydroxylase ("TH") stained tissue sample from the left stellate ganglion of an animal subject, showing a region of reduced staining following subcutaneous nerve stimulation.
Figure 12B:
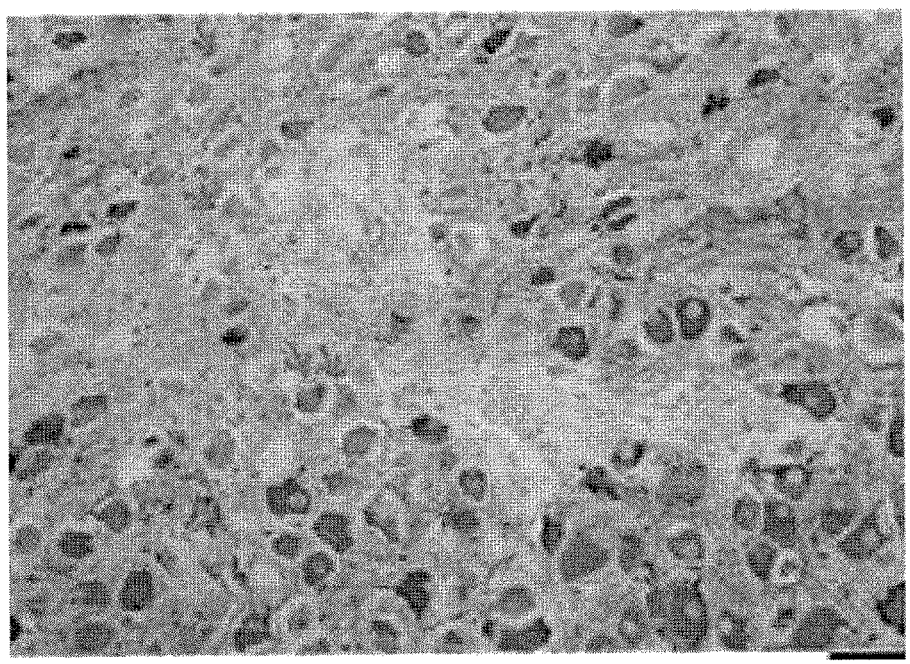
FIG. 12B is an enhanced image of the region shown in FIG. 12A.

As shown in the image of FIG. 12A, there is a region with reduced TH staining. A higher magnification view (FIG. 12 B) shows numerous TH-negative ganglion cells. Some of them have pyknotic nucleus. These findings suggest significant remodeling of the stellate ganglion. The reduced expression of TH and the pyknotic cells indicate that portion of the stellate ganglion was damaged by rapid pacing of the subcutaneous nerves. It was previously reported that vagal nerve stimulation can also significantly increase the TH-negative ganglion cells in the stellate ganglion, along with reduction of the SGNA. Therefore, it appears that the subcutaneous nerve stimulation can lead to the same stellate ganglion remodeling, which would result in reduced SGNA when the stimulation is turned off.

In summary, disclosed herein is a novel approach that utilizes measures and stimuli of the skin to monitor and/or control nerve activity of a subject. Specifically, a system and methods are provided for non-invasive or minimally invasive monitoring and/or controlling nerve activity using cutaneous and/or subcutaneous electrode configurations.

In some aspects, provided system and methods utilize measurements of electrical signals obtained via electrodes placed at specific locations on a subject's skin, in order to estimate a sympathetic nerve activity. Specifically, herein it is shown that nerve discharges recorded from the cutaneous and subcutaneous electrodes are correlated to stellate ganglion activity, and hence the present disclosure recognizes that such correlation may be utilized to estimate stellate ganglion activity from measured skin nerve activity.

The latter findings may also indicate that cutaneous and subcutaneous sympathetic nerves are directly connected to the stellate ganglion. Hence, the present disclosure also recognizes that such connection may be utilized to control stellate ganglion nerve activity. Hence, system and methods are provided which implement electrical stimulations to subcutaneous or cutaneous nerves in order to remodel specific neural structures, such as the stellate ganglion. As described, provided system and methods may be utilized to obtain similar therapeutic effects as the vagal nerve stimulation, by way of controlling stellate ganglion activity, but with much reduced risk to a subject. In some applications, reduced sympathetic outflow from the stellate ganglion may be used, for example, in treating various heart diseases, such as reducing the ventricular rate during atrial fibrillation or to reduce the incidence of cardiac arrhythmia.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A system for monitoring nerve activity in a subject, the system comprising:
    a plurality of electrodes configured for placement at locations proximate to a subject's skin;
    a signal detector configured to sample electrical signals detected by the plurality of electrodes; and
    a signal processor configured to:
        receive signal data corresponding to the electrical signals sampled by the signal detector;
        apply a filter to the received signal data to generate filtered signal data, the filter configured to attenuate at least signals having frequencies that correspond to heart muscle activity during a heartbeat, wherein the filter includes a high-pass filter with a cutoff frequency from 500 Hz to 700 Hz;
        assemble, using the filtered signal data, a waveform corresponding to a skin nerve activity;
        estimate a sympathetic nerve activity using the waveform corresponding to the skin nerve activity and a predetermined correlation, wherein the predetermined correlation relates skin nerve activity and sympathetic nerve activity;

generate a report indicative of the estimated sympathetic nerve activity.

2. The system of claim 1, wherein the plurality of electrodes are further configured to engage tissues in the subject comprising cutaneous nerves or subcutaneous arrangement nerves, or both.

3. The system of claim 1, wherein the signal detector further comprises signal amplifiers electrically connected to the plurality of electrodes, which configured to amplify the electrical signals detected to generate amplified signals.

4. The system of claim 1, wherein the sympathetic nerve activity comprises a stellate ganglion nerve activity.

5. The system of claim 1, wherein the signal processor is further configured to determine a medical condition of the subject using the estimated sympathetic nerve activity.

6. The system of claim 3, wherein the signal detector further comprises a sampler configured to generate the signal data at a rate of approximately 10,000 samples per second using the amplified signals.

\* \* \* \* \*